(12) United States Patent
Kitano et al.

(10) Patent No.: US 8,703,859 B2
(45) Date of Patent: Apr. 22, 2014

(54) PRODUCTION METHOD FOR WATER-ABSORBING RESIN COMPOSITION

(75) Inventors: Takahiro Kitano, Himeji (JP); Yorimichi Dairoku, Himeji (JP); Sumio Okuda, Ibo-gun (JP); Kozo Nogi, Kakogawa (JP); Motohiro Imura, Shiki-gun (JP)

(73) Assignee: Nippon Shokubai Co., Ltd., Osaka (JP)

( * ) Notice: Subject to any disclaimer, the term of this patent is extended or adjusted under 35 U.S.C. 154(b) by 568 days.

(21) Appl. No.: 11/725,496

(22) Filed: Mar. 20, 2007

(65) Prior Publication Data

US 2007/0225160 A1 Sep. 27, 2007

(30) Foreign Application Priority Data

Mar. 27, 2006 (JP) ................................ 2006-085637
Sep. 29, 2006 (JP) ................................ 2006-268936

(51) Int. Cl.
- *C08K 3/34* (2006.01)
- *C08L 31/00* (2006.01)
- *C08L 33/00* (2006.01)
- *C08L 33/02* (2006.01)

(52) U.S. Cl.
USPC ........................... 524/492; 524/543; 524/556

(58) Field of Classification Search
USPC ........................................ 524/492, 543, 556
See application file for complete search history.

(56) References Cited

U.S. PATENT DOCUMENTS

| | | | |
|---|---|---|---|
| 5,985,944 A | 11/1999 | Ishizaki et al. | |
| 6,124,391 A | 9/2000 | Sun et al. | |
| 6,300,275 B1 | 10/2001 | Weir | |
| 2002/0117259 A1* | 8/2002 | Giroux et al. | 156/330 |
| 2003/0020199 A1* | 1/2003 | Kajikawa et al. | 264/140 |
| 2003/0059521 A1 | 3/2003 | Gancet et al. | |
| 2004/0011414 A1* | 1/2004 | Ueberall | 138/39 |
| 2005/0113252 A1* | 5/2005 | Miyake et al. | 502/402 |
| 2005/0118423 A1 | 6/2005 | Adachi et al. | |
| 2006/0073969 A1 | 4/2006 | Torii et al. | |
| 2007/0125568 A1 | 6/2007 | Kida et al. | |

FOREIGN PATENT DOCUMENTS

| | | |
|---|---|---|
| CN | 1464826 A | 12/2003 |
| EP | 1 113 037 A2 | 7/2001 |
| EP | 0 629 411 B1 | 10/2001 |
| EP | 1 257 596 B1 | 11/2005 |
| EP | 1 741 835 A1 | 1/2007 |
| JP | 64-4653 | 1/1989 |
| JP | 9-241322 | 9/1997 |
| JP | 9 248454 | 9/1997 |
| JP | 10-120921 | 5/1998 |
| JP | 11-286611 | 10/1999 |
| JP | 2000-093792 | 4/2000 |
| JP | 2003-176421 | 6/2003 |
| JP | 2005081204 A * | 3/2005 |
| JP | 2005-097604 A | 4/2005 |
| JP | 2006-063300 A | 3/2006 |
| WO | 2005/010102 A1 | 2/2005 |
| WO | WO 2005/073469 A1 | 8/2005 |

OTHER PUBLICATIONS

Abstract of JP2005081204; Nogi et al; Mar. 2005.*
European Search Report dated Aug. 7, 2007.
Office Action from Chinese Patent Office issued in corresponding Chinese Patent Application No. 2007100882280 dated May 5, 2011, with a partial English translation thereof.
Office Action from the State Intellectual Property Office of P.R. China issued in corresponding Chinese Patent Application No. 200710088228.0 dated Sep. 27, 2010, with English Translation.
Extended European Search Report dated Dec. 29, 2010, issued by the European Patent Office in European Patent Application No. 10011717.5.
Official Action dated Dec. 28, 2010, issued by the Korean Patent Office in Korean Patent Application No. 10-2007-0027252, and English translation of the Official Action.
Taiwanese Office Action issued on Sep. 14, 2012, in corresponding Taiwanese Patent Application No. 096109462, and English translation thereof.
Official Action (Communication Pursuant to Article 94(2) EPC) dated Feb. 27, 2012, issued in corresponding European Application No. 10 011 717.5.

\* cited by examiner

*Primary Examiner* — Karuna P Reddy
(74) *Attorney, Agent, or Firm* — Buchanan Ingersoll & Rooney PC

(57) ABSTRACT

The present invention provides a method for being capable of sufficiently exerting property improvement effect by the addition of additive particles other than water-absorbing resin to water-absorbing resin particles. The problems can be solved by using additive particles having over cohesive particles in an amount equal to or less than a predetermined amount, or by using the additive particles by crushing or classifying in advance, before mixing with water-absorbing resin particles. Alternatively, the problem can be solved by subjecting a mixture of the water-absorbing resin particles and the additive particles to pneumatic transportation processing, in particular, in a heated state, after mixing or at the same time as mixing. Further, the present invention provides a water-absorbing resin composition, which is capable of stably exerting high-level property. The problems can be solved by a water-absorbing resin composition, where the addition amount of additive particles and amount of free additive particles satisfies a predetermined relation.

9 Claims, 1 Drawing Sheet

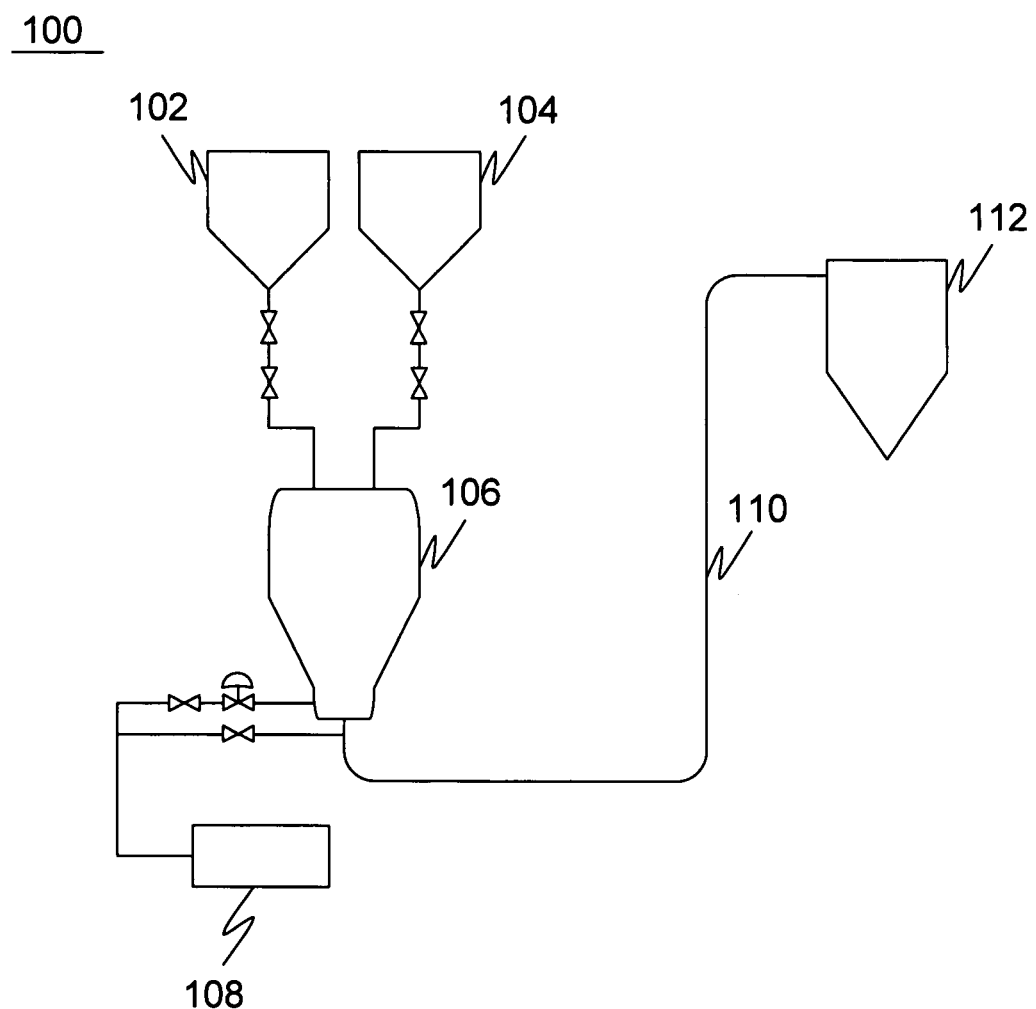

PRODUCTION METHOD FOR WATER-ABSORBING RESIN COMPOSITION

BACKGROUND OF THE INVENTION

1. Field of the Invention

The present invention relates to a production method for a water-absorbing resin composition. In more detail, the present invention relates to a production method for a water-absorbing resin composition, having a mixing step for mixing water-absorbing resin particles and additive particles.

2. Description of the Related Art

A water-absorbing resin, both a natural product and a synthesis product, generally has hydroscopicity, and as a natural product, starch and agar, or the like is known; and as a synthetic product, polyvinyl alcohol, polyacrylic acid (salt), polyacrylamide, polyethyleneimine, or the like is known.

A water-absorbing resin is widely used recently, aiming at absorbing body fluid, in the fields of hygienic goods such as a paper diaper or a sanitary napkin, so-called an in continence pad and the like. As such a water-absorbing resin, for example, partially neutralized cross-linked polyacrylic acid, a hydrolyzed starch-acrylonitrile graft polymer, a neutralized starch-acrylic acid graft polymer, a saponified vinyl acetate-acrylic acid ester copolymer, a hydrolyzed acrylonitrile copolymer or an acrylamide copolymer, or cross-linked body thereof, a cross-linked polymer of a cationic monomer or the like is known.

Characteristics which a water-absorbing resin should have includes water absorption characteristics such as excellent absorbency or absorption rate, and fluid permeability in contacting with aqueous fluid such as body fluid or the like, or handling property such as excellent fluidity so as not to adhere to apparatus or the like, even by moisture absorption, in preparation of an absorbing body by fabrication with a water-absorbing resin and a fiber substrate or the like, or in production or conveyance of a water-absorbing resin. Furthermore, with demand increase in an adult diaper accompanying the aging, characteristics for furnishing additional functions such as antibacterial or deodorant property to a water-absorbing resin has also been required.

To obtain various characteristics as described above, technology for the addition of additive particles aiming at furnishing various functions to water-absorbing resin particles has been proposed. For example, EP No. 629411, JP-A-2003-176421, and JP-A-11-286611 disclose technology to improve anti-gel-blocking property or fluid permeability of a diaper in absorbing urine; JP-A-2000-93792, U.S. Pat. No. 6,124,391, U.S. Pat. No. 5,985,944, JP-A-9-241322, JP-A-64-4653, and US-A-2005/113252 disclose technology to improve anti-caking characteristics; and WO-A-2005/10102, JP-A-9-248454, EP No. 1257596, and JP-A-10-120921 disclose technology for furnishing antibiotic property or deodorant property. In addition, because water-soluble resin particles similarly generate caking, similar solving methods by cohesive fine particles have been proposed. In addition, there are many proposals on methods for improving property by the addition of additive particles other than cohesive fine particles, to water-absorbing resin particles, for example, technology for the addition of powder of water-soluble metallic soap (US-A-2005/118423), or technology for the addition of powder of a polyvalent metal salt (US-A-2006/73969, U.S. Pat. No. 6,300,275), has been proposed.

And, as a mixing method for these additive particles and a water-absorbing resin, dryblend (mixing of power itself) is generally carried out, and many continuous type or batch type powder mixers have conventionally been proposed. As such powder mixers, for example, a paddle blender, a ribbon blender, a rotary blender, a jar-tumbler, a plunger mixer, a cylinder-type mixer, a V-shaped mixer, a ribbon-type mixer, a screw-type mixer, a double arm-type mixer, a crushing-type mixer, a channel-type mixer, a harrow-type mixer, an airflow type mixer and the like are known. In addition, in such mixing, a method for simultaneous granulating and mixing of a water-absorbing resin has been proposed (US-A-2006/73969)

BRIEF SUMMARY OF THE INVENTION

Although technology for mixing additive particles other than water-absorbing resin into water-absorbing resin particles is disclosed for many kinds of versatile objectives as above, many problems are still left at present.

Namely, techniques for improving anti-caking characteristics and the like by adding inorganic fine particles to a water-absorbing resin are known conventionally. However, the effect by the addition is not sufficient, and therefore, it is necessary to carry out mixing in a long term and to use a large amount of additive (inorganic fine particles) for the purpose of mixing the additive homogeneously, which involves deterioration in such properties as absorbency against pressure or enormous cost increase. Further, present inventors have found out that a water-absorbing resin obtained by a conventional method is not sufficient in view of long-term (for example, 5 hours) caking index, although the resin shows some effect in caking index for about 1 hour. Furthermore, it is also found that it is necessary to excel in view of long-term (for example, 5 hours) caking index for the purpose of the actual use such as a production of a diaper.

Accordingly, a first object of the present invention is to provide a water-absorbing resin composition and a method for producing the same capable of excelling in view of long-term (for example, 5 hours) caking index and capable of suppressing deterioration in absorption properties or cost increase in a water-absorbing resin composition made by the addition of an additive to a water-absorbing resin.

The present inventors have intensively studied a way to solve the above first object, and as a result, have found that a large quantity of over cohesive particles are present in conventional cohesive fine particles, which have a primary particle diameter of 3 to 500 nm and a cohesive particle diameter of about 1 to 40 μm, as described in a catalogue. In addition, it has also been found that presence of such over cohesive particles in a predetermined amount or more critically lowers property modification effect of a water-absorbing resin.

Based on such findings, the present inventors have found out that use of additive particles containing such over cohesive particles in a predetermined amount or less is capable of providing excellent property modification effect of a water-absorbing resin.

Namely, according to a first embodiment of the present invention, a method is provided for producing a water-absorbing resin composition, having a mixing step for mixing water-absorbing resin particles and additive particles, characterized in that rate of content of over cohesive particles, having a particle diameter of equal to or larger than 1.0 mm, in the additive particles, is equal to or smaller than 20% by weight.

In addition, the present inventors have found out that excellent property modification effect of a water-absorbing resin can be obtained also by crushing or classifying the additive particles in advance, before mixing with a water-absorbing resin, so as to reduce ratio of over cohesive particles contained in the additive particles, and by using such additive particles.

Namely, according to a second embodiment of the present invention, a method is provided for producing a water-absorbing resin composition, having a mixing step for mixing water-absorbing resin particles and additive particles, characterized by having a step for crushing or classifying the additive particles in advance, before the mixing step.

Furthermore, the present inventors have found out that excellent property modification effect of a water-absorbing resin can be obtained by subjecting a mixture of the water-absorbing resin particles and the additive particles to pneumatic transportation processing, in particular, in a heated state, after mixing or at the same time as mixing.

Namely, according to a third embodiment of the present invention, a method is provided for producing a water-absorbing resin composition, having a mixing step for mixing water-absorbing resin particles and additive particles, characterized in that a mixture of the water-absorbing resin particles and the additive particles is subjected to pneumatic transportation processing under a pressure of 0.1 to 10 MPa, in particular, in a heated state, after mixing or at the same time as mixing of the water-absorbing resin particles and the additive particles.

In addition, according to a fourth embodiment of the present invention, a method is provided for producing a water-absorbing resin composition, having a mixing step for mixing water-absorbing resin particles and additive particles, characterized in that a mixture of the water-absorbing resin particles and the additive particles is subjected to pneumatic transportation processing in plug flow, in particular, in a heated state, after mixing or at the same time as mixing of the water-absorbing resin particles and the additive particles.

On the other hand, there was conventionally a problem that, in application of a water-absorbing resin (a water-absorbing resin composition) to absorbing goods such as a diaper and the like, property of the absorbing goods is not necessarily-stable; namely, the resultant property fluctuates depending on the cases.

Accordingly, a second object of the present invention is to provide a water-absorbing resin composition, which is capable of stably exerting high-level property.

The present inventors have intensively studied a way to solve the above second object, and as a result, have found that, as one factor generating property fluctuation in conventional absorbing goods, distribution of a water-absorbing resin in the absorbing goods became non-uniform, in the case of practically incorporating a water-absorbing resin, after shipping, into absorbing goods such as a diaper (for example, in preparation of absorbing goods by mixing a water-absorbing resin and pulp and the like); and also found out that a water-absorbing resin composition, where the addition amount of additive particles and the amount of free additive particles satisfies a predetermined relation, is capable of stably expressing high-level property, and in particular, of expressing high absorbency against pressure and good anti-caking characteristics in a long term suitable for the production of a diaper.

Namely, according to a fifth embodiment of the present invention, a water-absorbing resin composition is provided, which contains 100 parts by weight of water-absorbing resin particles and 0.01 to 1 part by weight of additive particles, characterized in that percent by weight of the additive particles, (X [%]), based on 100% by weight of the water-absorbing resin particles in the composition, and weight ratio of free additive particles, (Y), relative to the percent by weight, (X [%]), satisfy the following formula:

$$0.04(x)^{0.1} \leq y \leq 0.2(x)^{0.5}$$

BRIEF DESCRIPTION OF THE DRAWINGS

FIG. 1 is an outline view showing one embodiment of a high concentration pneumatic conveying apparatus.

DETAILED DESCRIPTION OF THE INVENTION

Hereinafter, the present invention will be explained in detail by dividing into several embodiments, however, the scope of the present invention should be specified by description of claims, and should not be limited by the following specific embodiments.

A first embodiment of the present invention is a method for producing a water-absorbing resin composition, having the mixing step for mixing water-absorbing resin particles and additive particles, characterized in that rate of content of over cohesive particles, having a particle diameter of equal to or larger than 1.0 mm, in the additive particles, is equal to or smaller than 20% by weight.

(Water-Absorbing Resin Particle)

"A water-absorbing resin" represents a water-swelling, water-insoluble cross-linked polymer, which is capable of forming a hydrogel, and which absorbs water in an amount of 5 times of own weight, preferably, in an amount of 50 to 1,000 times of own weight in ion exchanged water, and contains water-soluble components (specified as content of an equilibrium extractable polymer, in U.S. reissued Pat. No. 32,649) in an amount of equal to or less than 50%, preferably, equal to or less than 25%. In addition, a water-absorbing resin is preferably a resin having a moisture absorption amount of equal to or more than 5% by weight of own weight when left for 1 hour under condition at a temperature of 25° C. and a humidity of 90% RH.

"A water-absorbing resin composition" represents particles (powder) consisting of any polymer which belongs to the concept of the water-absorbing resin above.

A water-absorbing resin used in the present invention includes partially neutralized cross-linked poly(meth)acrylic acid, a hydrolyzed starch-(meth)acrylonitrile graft polymer, a neutralized starch-(meth)acrylic acid graft polymer, a saponified vinyl acetate-(meth)acrylate ester copolymer, a hydrolyzed or cross-linked (meth)acrylonitrile copolymer or (meth)acrylamide copolymer, a cross-linked polymer of a cationic monomer or the like; among these, a water-absorbing resin is preferably to be partially neutralized cross-linked poly(meth)acrylic acid, and more preferably to be partially neutralized cross-linked polyacrylic acid, in view of excellent water absorption performance.

In addition, in the present invention, a water-soluble resin, which is a hydrophilic resin similarly as a water-absorbing resin, may be used instead of a water-absorbing resin. The water-soluble resin can be obtained without using an internal cross-linking agent and a surface cross-linking agent in the production method. The water-soluble resin includes, for example, polyacrylic acid or a salt thereof, or a copolymer thereof, exemplified in, for example, U.S. Pat. No. 5,064,563, U.S. Pat. No. 6,794,473, U.S. Pat. No. 6,521,721, U.S. Pat. No. 6,780,832 or the like. It is applicable to a water-soluble resin having a molecular weight, Mn, of usually, 500 to 10 million, preferably 1000 to 5 million, particularly, about 10,000 to 500,000, and in particular, dry powder. Embodiments of rate of water content or particle diameter of such powder are similar to those which will be described later on a water-absorbing resin.

A production step of water-absorbing resin particles (powder) will be explained below in the case where a water-absorbing resin is partially neutralized cross-linked polyacrylic acid.

To obtain partially neutralized cross-linked polyacrylic acid, a hydrophilic monomer, having acrylic acid and/or a salt thereof as a main component, may be polymerized; such polyacrylic acid is preferably a swollen and water-insoluble cross-linked polymer containing 30 to 100% by mole, preferably 50 to 100% by mole, more preferably 70 to 100% by mole, and particularly preferably 90 to 100% by mole of acrylic acid (salt) among repeating units (excluding a cross-linking agent). As a monomer other than acrylic acid (salt), hydrophilic monomers such as methacrylic acid, (anhydrous) maleic acid, fumaric acid, crotonic acid, itaconic acid, vinylsulfonic acid, 2-(meth)acrylamide-2-methylpropane sulfonic acid, (meth)acryloxyalkane sulfonic acid, N-vinyl-2-pyrolidone, N-vinylacetamide, (meth)acrylamide, N-isopropyl (meth)acrylamide, N,N-dimethyl(meth)acrylamide, 2-hydroxyethyl(meth)acrylate, methoxypolyethylene glycol (meth)acrylate, polyethylene glycol(meth)acrylate and the like, and salts thereof are specifically included. Neutralization rate is preferably 50 to 95% by mole, more preferably 60 to 90% by mole of the acid groups. The salt may be exemplified by an alkali metal salt, an ammonium salt, an amine salt or the like. To initiate polymerization, various polymerization initiators or activated energy rays such as ultraviolet rays or the like are used.

The polymerization initiators are not especially limited, and a thermally degradable type initiator or a photodegradable type initiator may be used. As a thermally degradable type initiator, persulfate such as sodium persulfate, potassium persulfate, ammonium persulfate or the like; peroxide such as hydrogen peroxide, t-butyl peroxide, methyl ethyl ketone peroxide or the like; azonitrile compound, or an azoamidine compound is included. As a photodegradable type initiator, a benzoin derivative, a benzil derivative, an acetophenone derivative, a benzophenone derivative, an azo compound or the like is included.

Other components may be added into a reaction system; for example, a hydrophilic polymer such as starch, a starch derivative, cellulose, a cellulose derivative, polyvinyl alcohol, polyacrylic acid (salt), cross-linked polyacrylic acid (salt); chain transfer agent, like hypophosphorous acid (salt); a chelating agent and the like may be added into a reaction system. In the case where a hydrophilic polymer is further added into a reaction system, the addition amount of the hydrophilic polymer is not especially limited, however, preferably 0 to 30% by weight, more preferably 0 to 10% by weight relative to the monomer. In the case where a chain transfer agent is further added into a reaction system, the addition amount of the chain transfer agent is not especially limited, however, preferably 0 to 1% by mole, more preferably 0.005 to 0.3% by mole relative to the monomer. In addition, in the case where a chelating agent is further added into a reaction system, the addition amount of the chelating agent is not especially limited, however, preferably 1 ppm by weight to 10% by weight, more preferably 10 to 800 ppm by weight, relative to the monomer.

In view of improving property of the resultant water-absorbing resin, polymerization is preferably reversed-phase suspension polymerization or aqueous solution polymerization, more preferably an aqueous solution polymerization. Further, stirring polymerization using a kneader and the like and stationary polymerization on a belt and the like are preferable as a form of the aqueous solution polymerization. In addition, the reversed-phase suspension polymerization is a method for polymerization of an aqueous monomer solution in a suspended state into a hydrophobic organic solvent, for example, as described in U.S. Pat. No. 4,093,776, U.S. Pat. No. 4,367,323, U.S. Pat. No. 4,446,261, U.S. Pat. No. 4,683,274, U.S. Pat. No. 5,244,735 or the like. On the other hand, the aqueous solution polymerization is a method for polymerization of an aqueous monomer solution without using a dispersing solvent, for example, as described in U.S. Pat. No. 4,625,001, U.S. Pat. No. 4,873,299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, U.S. Pat. No. 5,380,808, or EP No. 0811636, EP No. 0955086, EP No. 0922717 or the like. Monomers, cross-linking agents, polymerization initiators, and other additives described in these patents may also be used in the present invention. Monomers in polymerization are preferably in a state of an aqueous solution, and monomer concentration in the aqueous solution is preferably 10 to 70% by weight, and more preferably 20 to 60% by weight.

Temperature of polymerization initiation is not especially limited. A polymerization reaction may be advanced under foaming of a polymerization reaction solution, and the temperature of polymerization initiation may be equal to or higher than 90° C. On the other hand, in the case where a polymerization reaction is advanced under mild condition, the temperature of polymerization initiation may be about 20 to 95° C. Polymerization time is also not especially limited, however, about 1 sec to 10 hours is preferable, and about 1 sec to 6 hours is further preferable.

As a method for obtaining a cross-linked substance of the resultant partially neutralized polyacrylic acid by polymerization, a self-cross-linking without using a cross-linking agent may be adopted, however, a method for copolymerization or reaction of an internal cross-linking agent having 2 or more polymerizable unsaturated groups or reaction groups in 1 molecule is preferable.

A specific example of the internal cross-linking agent includes, for example, N,N'-methylene bis(meth)acrylamide, (poly)ethylene glycol di(meth)acrylate, (poly)propylene glycol di(meth)acrylate, trimethylolpropane tri(meth)acrylate, glycerin tri(meth)acrylate, glycerin acrylate methacrylate, ethylene oxide modified trimethylolpropane tri(meth)acrylate, pentaerythritol tetra(meth)acrylate, triallyl cyanurate, triallyl isocyanurate, triallyl phosphate, triallyl amine, poly(meth)allyoxy alkane, (poly)ethylene glycol diglycidylether, glycerol diglycidylether, ethyleneglycol, polyethylene glycol, propylene glycol, glycerin, pentaerythritol, ethylenediamine, ethylene carbonate, propylene carbonate, polyethyleneimine, glycidyl(meth)acrylate or the like. These internal cross-linking agents may be used alone or in combination of 2 or more kinds.

Use amount of the internal cross-linking agent is not especially limited, however, preferably 0.005 to 3% by mole, and more preferably 0.01 to 1.5% by mole relative to 100% by mole of the monomer components. The use amount of the internal cross-linking agent equal to or more than 0.005% by mole is capable of suppressing reduction of fluid permeability or absorption rate of the resultant water-absorbing resin. On the other hand, the use amount of the internal cross-linking agent equal to or less than 3% by mole is capable of suppressing reduction of absorbency of the resultant water-absorbing resin.

The resultant polymer by the above polymerization is usually a water-containing polymer. In an aqueous solution polymerization, the water-containing polymer is recovered, and is preferably crushed using a crusher at the time of polymerization and after polymerization. The crusher is not especially limited. In addition, methods other than a crusher may be used as long as being capable of crushing. As the crusher, for example, a screw-type extruder such as a kneader (manufactured by Moriyama Co., Ltd.), a meat chopper (manufactured by Hiraga Kosakusho Co., Ltd.), or Dome Granulator (manufactured by Fuji Paudal Co., Ltd.) and the like, or a vertical-type crusher like Roatplex (manufactured by Hosokawa Micron Group) and the like may be used.

Average particle diameter of the water-containing polymer after crushing or after polymerization is preferably equal to or smaller than 100 mm, more preferably equal to or smaller than 10 mm, further preferably equal to or smaller than 3 mm, and particularly preferably equal to or smaller than 1 mm. It is ideal that crushing is possible to final product size in a water-containing polymer state.

The crushed water-containing polymer is dried to be a base polymer. The drying method is not especially limited and a suitable drier may be selected in response to solid content or particle diameter of the water-containing polymer. The drying method is not especially limited, however, such a drying method is preferably used that the water-containing polymer is well contacted with hot air or a heat transfer surface while moving the water-containing polymer, such as an azeotropic distillation method, a stirring drying method, a fluid bed drying method, an airflow drying method or the like. Medium used for drying includes hot air, infrared ray, microwave or the like. A ventilator and the like may be used as long as sufficient drying can be attained without heating. Drying temperature in the case of drying by heating is not especially limited, however, preferably 70 to 250° C., and more preferably 120 to 230° C.

In addition, "drying" in the present invention is a concept widely including the step for increasing solid content of the water-containing polymer. Water content of the base polymer after drying is not especially limited; however, drying is preferably carried out so as to obtain a solid content (at 180° C. for 3 hours) of 90 to 100% by weight.

The dried base polymer is classified and the base polymer having suitable particle diameter is supplied to the step for surface cross-linking to be described below. The classification method is not especially limited. Narrower particle diameter distribution of the base polymer after classification improves various characteristics such as absorption performance and the like. In addition, shape of the base polymer is not especially limited, and any shape such as spherical, scale-like, indeterminate crushed-like, granulate-like shape or the like may be adopted. The same applies also to a water-absorbing resin after surface cross-linking.

The base polymer having particle diameter without this range is preferably subjected to particle size control and reuse so as to improve productivity of a water-absorbing resin. The base polymer having too large particle diameter is crushed using a crusher such as a roll mill or the like, and is charged again to a classification machine. Fine powder-like base polymer is charged to a crusher, after granulation. Granulation methods are not especially limited, and various known technologies may be applied.

As described above, in the present invention, water-absorbing resin particles (powder) are particularly preferably to be a water-absorbing resin after surface cross-linking. A water-absorbing resin after surface cross-linking is obtained by subjecting to cross-linking processing at the vicinity of the surface of the above base polymer.

A surface cross-linking agent used for surface cross-linking of the base polymer includes, for example, an oxazoline compound (U.S. Pat. No. 6,297,319), a vinyl ether compound (U.S. Pat. No. 6,372,852), an epoxy compound (U.S. Pat. No. 6,265,488), an oxetane compound (U.S. Pat. No. 6,809,158), a polyhydric alcohol compound (U.S. Pat. No. 4,734,478), a polyamideamine-epihalo adduct (U.S. Pat. No. 4,755,562 and U.S. Pat. No. 4,824,901), a hydroxyl acrylamide compound (U.S. Pat. No. 6,239,230), an oxazolidinone compound (U.S. Pat. No. 6,559,239), a bis- or poly-oxazolidinone compound (U.S. Pat. No. 6,472,478), a 2-oxotetrahydro-1,3-oxazolidinone compound (U.S. Pat. No. 6,657,015), an alkylene carbonate compound (U.S. Pat. No. 5,672,633) or the like. These surface cross-linking agents may be used alone or in combination of 2 or more kinds. In addition, with these cross-linking agents, a water-soluble cation such as an aluminum salt or the like (U.S. Pat. No. 6,605,673, U.S. Pat. No. 6,620,899) may be used in combination; or alkali (US-A-2004/106745), an organic acid or an inorganic acid or the like (U.S. Pat. No. 5,610,208) may be used in combination. In addition, polymerization of a monomer may be carried out at the surface of the base polymer to yield a water-absorbing resin after surface cross-linking (US-A-2005/48221).

As a surface cross-linking agent, a polyhyric alcohol compound, a polyvalent epoxy compound, a polyvalent amine compound and salt thereof, or an alkylene carbonate compound is preferably used. A specific example of a surface cross-linking agent includes, for example, a polyhydric alcohol compound such as (di, tri, tetra, poly)ethyleneglycol, (di, poly)propylene glycol, 1,3-propanediol, 2,2,4-trimethyl-1,3-pentanediol, (poly)glycerin, 2-butene-1,4-diol, 1,4-butanediol, 1,3-butanediol, 1,5-pentanediol, 1,6-hexanediol, trimethylolpropane, di- or tri-ethaolamine, pentaerythritol, solbitol or the like; an epoxy compound such as (poly)ethylene glycol diglycidyl ether, (di, poly)glycerol polyglycidyl ether, (di, poly)propylene glycol diglycidyl ether, glycidol or the like; a polyvalent oxazoline compound like 1,2-ethylene bisoxazoline; an alkylene carbonate compound like 1,3-dioxolane-2-one; a polyvalent metal compound like aluminum sulfate or the like is included.

Use amount of the surface cross-linking agent is not especially limited, however, preferably 0.01 to 10% by weight, more preferably 0.5 to 5% by weight, relative to 100% by weight of the base polymer. The use amount of the surface cross-linking agent equal to or more than 0.01% by weight is capable of suppressing reduction of fluid permeability of the resultant water-absorbing resin after surface cross-linking. On the other hand, the use amount of the surface cross-linking agent equal to or less than 10% by weight is capable of suppressing reduction of absorbency of the resultant water-absorbing resin after surface cross-linking.

In addition, the step for surface cross-linking may be carried out 2 times or more in consideration of the effect; in this case, a surface cross-linking agent used in each of the steps for surface cross-linking maybe the same or different each other.

In the step for surface cross-linking, the heating processing is preferably carried out to a mixture of the base polymer and the surface cross-linking agent, in a mixed state thereof. In this way, a cross-linking structure can efficiently be introduced to the surface of the base polymer particles.

The heating method is not especially limited, and a usual dryer or a heating furnace may be used. For example, a thin stirring type dryer, a rotation dryer, a disk dryer, a fluid bed dryer, a airflow dryer, an infrared dryer or the like may be used as the heating method. Temperature for heat processing is also not especially limited, however, preferably 40 to 250° C., more preferably 90 to 230° C., and further preferably 120 to 220° C. The temperature for heat processing equal to or higher than 40° C. is capable of suppressing reduction of retention rate of fine powder. On the other hand, the temperature for heat processing equal to or lower than 250° C. is capable of suppressing thermal degradation of a water-absorbing resin. Time for heat processing is also not especially limited, however, preferably 1 to 120 minutes, and more preferably 10 to 60 minutes.

In the present invention, in producing water-absorbing resin particles (power), a granulation step may be carried out in addition to the above steps. The granulation step is carried out before or after the surface cross-linking step, or at the same time as the surface cross-linking step.

In the granulation step or the surface cross-linking step, an aqueous solution dissolved with various additive components is added to a water-absorbing resin. Such additive components include, for example, chelating agent (diethylenetriamine pentaacetate, triethylenetetramine hexaacetic acid, cyclohexane-1,2-diamine tetraacetic acid, N-hydroxyethyl-ethylenediamine triacetic acid, ethylene glycol diethyl ether diamine tetraacetic acid, and the like), plant constituent (tannin, tannic acid, galla, gallnut, gallic acid, and the like), inorganic salt (polyvalent metal salt such as calcium, aluminum, magnesium, zinc and the like) and the like.

The addition amount of water in the granulation step is preferably 2 to 8% by weight, more preferably 3 to 5% by weight, relative to 100% by weight of a water-absorbing resin. A method for granulation is not especially limited, however, the method for granulation preferably has high mixing force. From such a viewpoint, a preferable granulation apparatus includes, for example, a cylinder-type mixer, a double wall cone mixer, a high speed stirring type mixer, a V-shaped mixer, a continuous type Rhedige mixer, a turbulizer or the like.

Production of water-absorbing resin particles (powder) via the above-described granulation step sometimes generates granules having a particle diameter over 1 mm; such granules are not suitably applied to hygienic goods such as a paper diaper because commingling of such granules causes stiff feeling in wearing thereof, or could break the top sheet of a diaper. Therefore, water-absorbing resin particles (powder) containing such large granules are subjected to granulate so as to make particle diameter smaller, namely, crushing/classification to a particle diameter equal to or smaller than a predetermined level.

Particle diameter of the resultant water-absorbing resin after surface cross-linking is not especially limited, however, weight average particle diameter (D50) of the water-absorbing resin after surface cross-linking is preferably 200 to 710 μm, more preferably 200 to 600 μm, and further preferably 200 to 500 μm. The weight average particle diameter equal to or larger than 200 μm is preferable in view of fluid permeability or anti-caking characteristics; and the weight average particle diameter equal to or smaller than 710 μm is preferable in view of absorption rate. In addition, in view of various absorption performances such as absorbency against pressure or liquid dispersing capability and the like, total content of water-absorbing resins after surface cross-linking, having a particle diameter of equal to or larger than 850 μm, and equal to or smaller than 150 μm is preferably 0 to 5% by weight, more preferably 0 to 4% by weight, and further preferably 0 to 1% by weight, relative to 100% by weight of total amount of water-absorbing resin particles (power). Furthermore, logarithmic standard deviation ($\sigma\zeta$) of the particle size distribution is preferably 0.20 to 0.50, more preferably 0.25 to 0.45, and further preferably 0.28 to 0.40. In addition, parameter value on these particle diameters is in accordance with US-A-2005/118423, and a value measured by a standard sieve classification (JIS Z8801-1 (2000) or a sieve equivalent thereto) should be adopted.

Bulk specific gravity (specified by JIS K-3362-1998) of the resultant water-absorbing resin after surface cross-linking is preferably 0.40 to 0.90 g/ml, more preferably 0.50 to 0.85 g/ml and most preferably 0.60 to 0.80 g/ml.

In addition, as fluid permeability, SFC (see US-A-2004/254553) of the resultant water-absorbing resin after surface cross-linking is usually equal to or larger than $1\times10^{-7}$ ($cm^3\times sec/g$), preferably equal to or larger than $10\times10^{-7}$ ($cm^3\times sec/g$), further preferably equal to or larger than $50\times10^{-7}$ ($cm^3\times sec/g$), and most preferably equal to or larger than $100\times10^{-7}$ ($cm^3\times sec/g$).

Furthermore, in absorbency against pressure of the resultant water-absorbing resin after surface cross-linking, value of PPUP is preferably 40 to 100%, more preferably 50 to 100%, further preferably 60 to 100%, and most preferably 70 to 100%. In addition, PPUP is described in WO06/109844, and specifically measured by the following method.

Permeability performance under pressure (PPUP) of the water-absorbing resin after surface cross-linking is specified by the following equation:

$$PPUP(\%)=[(AAP:5.0\ g)/(AAP:0.90\ g)]\times 100$$

where "AAP: 0.90 g" represents absorbency against pressure for 0.90 g of the water-absorbing resin after surface cross-linking; and "AAP: 5.0 g" represents absorbency against pressure for 5.0 g of the water-absorbing resin after surface cross-linking, in absorbency against pressure for 60 minutes to an aqueous solution of sodium chloride of 0.90% by weight, under a pressure of 4.8 kPa.

Here, specifications on the above-described weight average particle diameter or ratio of a resin having predetermined particle diameter, bulk specific gravity, fluid permeability and PPUP may be applied not only to a water-absorbing resin after surface cross-linking but also to a base polymer; namely, in the case where the above-described base polymer is used as water-absorbing resin particles (powder), weight average particle diameter or ratio of a resin having predetermined particle diameter, bulk specific gravity, fluid permeability and PPUP of the base polymer are preferably within the above-described range on the water-absorbing resin after surface cross-linking, from the same reason. In addition, in the present invention, as value of weight average particle diameter or ratio of a resin having predetermined particle diameter, value calculated by a method described in Examples to be referred to below should be adopted.

In addition, centrifuge retention capacity (CRC) of water-absorbing resin particles (powder) used in the present invention to a saline solution (an aqueous solution of sodium chloride of 0.90% by weight) is preferably equal to or higher than 25 g/g, more preferably 25 to 80 g/g, and further preferably 25 to 50 g/g. CRC value within such a range is preferable in view of excellent in performance in applications as hygienic goods. In addition, in the present invention, as CRC value, value measured by the method described in Examples to be referred to below.

In addition, absorbency against pressure of water-absorbing resin particles (powder), used in the present invention, to a saline solution, is preferably 10 to 50 g/g, more preferably 15 to 50 g/g, and further preferably 20 to 50 g/g. In an exemplary embodiment, the absorbency against pressure at 0.3 psi is equal to or larger than 10 [q/q]. Absorbency against pressure value within such a range is preferable in view of excellent performance in applications to hygienic goods. In addition, in the present invention, as absorbency against pressure value, value measured by a method described in Examples to be referred to below should be adopted.

Furthermore, caking index of water-absorbing resin particles (powder), used in the present invention is preferably 0 to 50%, more preferably 0 to 30%, and further preferably 0 to 10%. Caking index ithin such a range is preferable in view of excellent handling in a high-humidity environment in actual use (particularly in the production of a diaper). In addition, in the present invention, as caking index, value measured by a method described in Examples to be referred to below should be adopted.

(Additive Particles)

In the present invention, the above-described water-absorbing resin particles (powder) are mixed with additive particles other than water-absorbing resin. Preferable embodiments of the additive particles will be explained below, however, the scope of the present invention is by no means limited only to the following embodiments.

Specific embodiments of the additive particles are not especially limited as long as being such powder that is capable of furnishing various functions to the water-absorbing resin particles (powder) by mixing with the water-absorbing resin particles (powder), and conventional knowledge may be referred to as appropriate.

In the present invention, the additive particles are preferably cohesive fine particles. The following explanation will be on an example of the case where the additive particles are cohesive fine particles, however, the scope of the present invention is by no means limited to such embodiments, and additive particles other than cohesive fine particles to be described later may be adopted.

"Cohesive fine particles" represent highly cohesive fine particles having an average primary particle diameter of 3 to 500 nm, and ratio of cohesive particles having a cohesive particle diameter below 53 μm, is below 50% by weight relative to total amount of the cohesive fine particles. Here, the average primary particle diameter is preferably 5 to 100 nm, and more preferably 10 to 50 nm. In addition, as the above-described average primary particle diameter value, value measured by a Coulter counter method should be adopted. In addition, as ratio value of cohesive particles having the above predetermined particle diameter, value measured by the following method should be adopted.

[A Measurement Method for Ratio of Cohesive Particles Having a Cohesive Particle Diameter Below 53 μm]

Under condition of a temperature of 23° C. and a humidity of 50% RH, 50.0 g of cohesive fine particles were charged onto JIS standard sieves, Z8801-1, with a mesh opening of 53 μm (made of stainless: inner diameter=200 mm, depth=45 mm), and then subjected to classification for 5 minutes using a Ro-Tap type sieving vibrator for 200φ (manufactured by IIDA SEISAKUSHO Co., Ltd.: number of vibration=290 r/m, number of hammer=165 r/m, 100 V, 60 Hz).

Cohesive fine particles may be water-soluble fine particles of polyvalent metal salts and the like, or may be water-insoluble fine particles; preferably, cohesive fine particles are water-insoluble or water-hardly-soluble. In addition, solubility in 100 g of water at 23° C. is essentially less than 1 g, preferably less than 0.01 g, more preferably less than 0.0001 g.

Apparent bulk specific gravity of cohesive fine particles is not especially limited, however, preferably 0.01 to 1 g/cm$^3$, more preferably 0.02 to 0.5 g/cm$^3$ and further preferably 0.02 to 0.3 g/cm$^3$. Apparent bulk specific gravity value of cohesive fine particles within such a range is preferable in view of providing excellent dispersion property of cohesive fine particles. In addition, as apparent bulk specific gravity value of cohesive fine particles, value measured by a method specified in JIS K-3362-1998 should be adopted.

BET specific surface area of cohesive fine particles is not especially limited, however, preferably 1 to 10000 m$^2$/g, more preferably 10 to 1000 m$^2$/g, and further preferably 50 to 500 m$^2$/g. In addition, pH of an aqueous solution dissolved with cohesive fine particles, or a dispersion solution dispersed with cohesive fine particles, is usually 2 to 12.

Drying loss of cohesive fine particles (at 180° C. for 3 hours) is also not especially limited, however, preferably 0 to 15% by weight, more preferably 0 to 10% by weight, further preferably 0 to 5% by weight, and particularly preferably 0 to 1% by weight. Drying loss value within such a range is preferable in view of providing excellent dispersing property or mixing property of cohesive fine particles. In addition, as drying loss value of cohesive fine particles, value measured by the following method should be adopted.

[A Measurement Method for Drying Loss of Cohesive Fine Particles]

At the bottom surface of an aluminum dish (weight: Wa (g)), having a bottom surface diameter of 52 mm and a height of 22 mm, 1.00 g of a sample of cohesive fine particles is uniformly sprayed. Then, the dish containing the sample is dried in a calm dryer at 180° C. for 3 hours to measure weight thereof after drying (Wb (g)). Drying loss (% by weight) is calculated from theses weights, Wa and Wb, according to the following equation:

$$\text{Drying loss(\% by weight)} = (1 + Wa - Wb) \times 100$$

Specific examples of cohesive fine particles include, for example, inorganic fine particle-like powder such as silica (silicon dioxide), titania (titanium dioxide), alumina (aluminum oxide), magnesia (magnesium oxide), zinc oxide, talc, calcium phosphate, barium phosphate, clay, diatomite, zeolite, bentonite, kaolin, hydrotalcite, activated clay and the like; and organic fine particle-like powder such as cellulose, pulp, ethyl cellulose, ethylhydroxyethyl cellulose, cellulose acetate butyrate, modified starch, chitin, rayon, polyester, polyethylene, polypropylene, polyvinyl chloride, polystyrene, nylon, polymethyl methacrylate, melamine resin, a melamine-benzoguanamine resin, activated carbon, tea-leaf and the like. These cohesive fine particles may be used alone or in combination of 2 or more kinds.

Among these cohesive fine particles, water-insoluble inorganic fine particle-like powder is preferable, more preferably in an amorphous state, and further preferably, silica, titania, alumina, zeolite, kaolin, and hydrotalcite are used, and particularly preferably, silica is used. As commercially available products thereof, trade name, "Cypernut", manufactured by Degussa Co.; trade name, "Carprex", manufactured by Shionogi & Co., Ltd.; trade name, "Aerosil 200, Aerosil 200CF, Aerosil 300, Aerosil 300CF, Aerosil 380, Aerosil R972", manufactured by Japan Aerosil Co.; and trade name, "Reolosil QS-20", manufactured by Tokuyama Corp. and the like are included.

In addition, the surface of cohesive fine particles may contain an anionic group, a cationic group, an alkyl group or the like, or maybe modified to be hydrophilic or hydrophobic. Among these, containing a cationic group (an amine group) at the surface is preferable. Such cohesive fine particles specifically include "RA200HS" manufactured by Japan Aerosil Co.; "HDK" (trademark) series, "H2015EP", "H2050EP", "H2150VP", "H05TA", "H13TA", and "H30TA", manufactured by WACKER Co., Ltd.; and the like.

The first embodiment of the present invention is characterized by using additive particles (cohesive fine particles) having small content of over cohesive particles. Here, "over cohesive particles" represent cohesive particles having a particle diameter of equal to or larger than 1.0 mm. Such over cohesive particles may be generated by local pressure loaded in producing, filling after production, or conveyance after production of cohesive fine particles. The present inventors have found that cohesive fine particles represented by trade name, "Aerosil 200" (manufactured by Japan Aerosil Co., having a primary particle diameter of 12 nm) are unexpectedly cohesive as described above, and in addition, have ratio of over cohesive particles, to be described later, as large as equal to or more than 40% by weight (the upper limit is 100% by weight), and this adversely affect property modification of a water-absorbing resin; and on the contrary, small rate of content of over cohesive particles sufficiently exerts property modification effect by the addition of additive particles to water-absorbing resin particles.

In the first embodiment, rate of content of over cohesive particles in additive particles (cohesive fine particles) is 0 to 20% by weight, preferably 0 to 10% by weight, more preferably 0 to 5% by weight, and further preferably 0 to 2% by weight. According to such an embodiment, surface property modification effect of water-absorbing resin particles (powder) by mixing water-absorbing resin particles (powder) and additive particles maybe improved. In addition, as rate of content value of over cohesive particles in additive particles (cohesive fine particles), value measured by a method referred to in Examples to be described below should be adopted.

Cohesive fine particles, having ratio of over cohesive particles within the above range, maybe obtained by adjusting the production step of cohesive fine particles, or by selecting from a plurality of lots of cohesive fine particles, however, because of possibility of re-cohesion, it is preferable that ratio of over cohesive particles is set to a desired value by crushing/classification of cohesive fine particles, in advance, before the mixing step to be described later. In addition, "crushing" represents an operation for flaking cohesion and it is not necessary for the crushing to involve pulverization, in general.

Namely, the second embodiment of the present invention is a method for producing a water-absorbing resin composition, having a mixing step for mixing water-absorbing resin particles and additive particles, characterized by having a step for crushing or classifying the additive particles in advance, before the mixing step.

Methods for crushing/classification of cohesive fine particles are not especially limited; however, the following methods (a) to (d) are preferable.

(a) Crushing/Classification by Passing Through a Screen Mesh or a Perforated Plate Opening of a screen mesh to be used is not especially limited, however, a standard screen with an opening of equal to or smaller than 5 mm is preferable, more preferably equal to or smaller than 2 mm, further preferably equal to or smaller than 1.5 mm, and particularly preferably equal to or smaller than 1.0 mm. In addition, number of passing time or piece through the screen mesh may be once (1 piece), or twice (2 pieces); and may be adjusted as appropriate, in response to length of a conveying tube, conveying capability of a pump, screen mesh opening or the like. In addition, for the same purpose, a plate having a number of openings (namely, a perforated plate) may be used. Preferable range of diameter of the openings in the perforated plate is the same as the range of the openings in the screen mesh described above.

(b) Crushing by Airflow

Airflow, for example, airflow of 0.1 to 100 m/sec is blown to 1 kg of fine particles for about 1 second to 10 hours, preferably about 1 minute to 1 hour. In addition, the airflow may be generated under pressure or by aspiration.

(c) Crushing by Stirring

Stirring is executed using a stirring blade in 10 to 10000 rpm, preferably 100 to 5000 rpm, for about 1 second to 10 hours, preferably about 1 minute to 1 hour.

(d) Crushing by a Crusher

Crushing is executed using, for example, a meat chopper, Dome Granulator (wet-process extrusion granulator), "Allgaier" (oscillating type cylinder sieve), a vibration sieving apparatus, jet mill, flash mill, pin mill, roll mill, hammer mill, cutter mill, homogenizer, sample mill or the like.

In addition, in the step for crushing/classification of over cohesive fine particles, utilization of energy used in conveying (filling) of cohesive fine particles to a supply hopper is preferable, and crushing/classification may be executed at the same time with conveyance. For example, in the case where cohesive fine particles are filled to the supply hopper by an aired pump (an air drive type diaphragm pump for powder), a method for installing a screen mesh in a conveying tube for filling, so as to crush by subjecting cohesive fine particles to pass through the screen mesh, is particularly preferable. In the case where setting of the screen mesh makes difficult flow of cohesive fine particles through the conveying tube, good flow is obtained, in many cases, by increasing air amount to be supplied to the conveying tube.

Specific explanation was given above on the case where additive particles are cohesive fine particles, as an example, however, powder other than cohesive fine particles may be used as "additive particles". Powder other than cohesive fine particles, which may be used as "additive particles", includes, for example, a monovalent metallic salt, like sodium chloride; a multivalent metallic salt, like aluminum sulfate; a sulfur-containing inorganic compound such as sodium sulfite, sodium hydrogen sulfite or the like (U.S. Pat. No. 4,863,989); apatite; polyoxyethylene alkyl ether, metallic soap, like stearate; a surfactant, like sorbitan fatty acid ester; a water-soluble polymer such as polyethylene oxide, poly(meth)acrylic acid (salt), polyvinyl pyrrolidone or the like; an organic acid (salt) such as L-ascorbic acid (salt), oxalic acid (salt), succinic acid (salt) or the like; a radical inhibitor such as hydroquinone, methoquinone or the like (U.S. Pat. No. 4,972,019); a chelating agent such as ethylenediamine tetraacetic acid (salt), diethylenepentamine pentaacetic acid (salt), ethylenediamine disuccinic acid (salt) or the like (U.S. Pat. No. 6,599,989); cyclodextrin; an inorganic bacteriacide such as silver, cupper, zinc or the like, however, particles (powder) other than these may also be used naturally as "additive particles". In addition, the same range as the range described above relating to the cohesive fine particles is applied to apparent bulk specific gravity, BET specific surface area, drying loss, over cohesive particles (cohesive particles having a particle diameter equal to or larger than 1.0 mm) and the like of the above additive particles other than cohesive fine particles.

By mixing additive particles, various functions depending on additive particles can be furnished to water-absorbing resin particles (powder). In this case, specific functions furnished to water-absorbing resin particles (powder) are not especially limited, and conventionally known knowledge such as obtainable from the above each Patent Literature or the like may be referred to, as appropriate. As one example, adoption of silica or metallic soap as additive particles improves performance such as anti-caking characteristics of water-absorbing resin particles (powder). In addition, adoption of silica or aluminum sulfate as additive particles improves performance such as fluid permeability of water-absorbing resin particles (powder). Furthermore, adoption of titanium oxide or cyclodexitrin as additive particles may furnish deodorizing function or the like to water-absorbing resin particles (powder).

(A Mixing Step of Water-Absorbing Resin Particles and Additive Particles)

In the present invention, it is preferable that a mixture of water-absorbing resin particles (powder) and additive particles is subjected to pneumatic transportation processing, in a heated state, after mixing or at the same time of mixing, preferably after mixing, more preferably just after mixing. In the present invention, "a mixture is subjected to pneumatic transportation processing" represents that a mixture of water-absorbing resin particles (powder) and additive particles are supplied to an apparatus, which is capable of moving the mixture under a pressure of 0.1 to 10 MPa, or generates plug flow, so as to move the mixture, under predetermined pressure condition, or while forming plug flow. Plug flow is generated by pneumatic transporting of compressed air into an apparatus for processing the mixture (usually a piping). Pressure value of compressed air used in this case is 0.1 to 10 MPa. Pressure of compressed air within such a range effectively mixes water-absorbing resin particles (powder) and additive particles, by efficient generation of plug flow. Uniform mixing of water-absorbing resin particles (powder) and additive particles completes a water-absorbing resin composition. In addition, "just after mixing" represents within 0 to 120 minutes after mixing, preferably within 0 to 60 minutes after mixing, and more preferably within 0 to 20 minutes after mixing, for pressure feeding.

Namely, the third embodiment of the present invention is a method for producing a water-absorbing resin composition, having a mixing step for mixing water-absorbing resin particles and additive particles, characterized in that a mixture of the water-absorbing resin particles and the additive particles is subjected to pneumatic transportation processing under a pressure of 0.1 to 10 MPa, in particular, in a heated state, after mixing or at the same time as mixing of the water-absorbing resin particles and the additive particles.

In addition, the fourth embodiment of the present invention is a method for producing a water-absorbing resin composition, having a mixing step for mixing water-absorbing resin particles and additive particles, characterized in that a mixture of the water-absorbing resin particles and the additive particles is subjected to pneumatic transportation processing in plug flow, in particular, in a heated state, after mixing or at the same time as mixing of the water-absorbing resin particles and the additive particles.

In the present invention, concept of "mixing by plug flow processing" is not limited in any way except that water-absorbing resin particles (powder) and additive particles are mixed while forming plug flow, and should be construed in the maximal range. However, plug flow processing is preferably carried out at the same time as pneumatic conveyance. The present invention will be explained in more detail below on the case where a mixture of water-absorbing resin particles (powder) and additive particles is subjected to plug flow processing at the same time as high concentration pneumatic conveyance, as an example, however, the scope of the present invention should be specified based on claims, and should by no means limited only to the following embodiments.

Preferable embodiments of the mixing step in the third and fourth embodiments of the present invention will be explained with reference to FIG. 1. A high concentration pneumatic conveyance apparatus may be designed by referring to known technology such as described in JP-A-6-191640, JP-A-6-345264, "16.6.2 A convey method by fluid" in "Handbook of Chemical Engineering" page 890, edited by The Society of Chemical Engineers, Japan, and published by Maruzen Co., Ltd.

FIG. 1 is an outline view showing one embodiment of the high concentration pneumatic conveyance apparatus 100. Water-absorbing resin particles (powder) are stored in the first hopper 102. On the other hand, additive particles are stored in the second hopper 104. Each of water-absorbing resin particles (powder) stored in the first hopper 102, and additive particles stored in the second hopper 104 is supplied to the lift tank 106. In supplying water-absorbing resin-particles (powder) and additive particles from each of the hoppers (102, 104) to the lift tank 106, compressed air prepared by the compressor 108 is used. It is preferable that a gas-sealing valve is installed at the bottom part of each of the hoppers (102, 104).

In the lift tank 106, water-absorbing resin particles (powder) and additive particles contact and mixing thereof is started. In this case, a mixing state of water-absorbing resin particles (powder) and additive particles inside the lift tank 106 is not especially limited; it may be an inhomogeneous mixture state in a degree distinguishable by a visual inspection, or a homogeneous mixture state. A mixing unit (not shown) may separately be installed in the lift tank 106, aiming at providing a homogeneous mixture inside the lift tank 106. Operation mechanism of such a mixing unit is not especially limited, however, for example, stirring mixing or airflow mixing is exemplified, and in particular, airflow mixing may preferably be adopted. In the case where stirring mixing is adopted, for example, a stirring blade is installed inside the lift tank. On the other hand, in the case where airflow mixing is adopted, for example, a blower which is capable of generating airflow in a circumference direction of the lift tank is installed at the inner wall of the lift tank. In addition, according to the present invention, because homogeneous mixing between water-absorbing resin particles (powder) and additive particles can be attained by high concentration pneumatic conveyance processing to be described in detail below, it is preferable that such a separate mixing unit is not installed in view of production cost reduction or compact sizing of production equipment. Namely, in the third and fourth embodiments of the present invention, it is preferable that water-absorbing resin particles (powder) and additive particles are mixed without stirring, and are subsequently subjected to pneumatic transportation processing.

The above-described mixture is supplied to the conveying tube 110 via the lift tank 106. Also in supplying a mixture to the conveying tube 110 from the lift tank 106, and conveyance of the mixture inside the conveying tube 110, compressed air prepared by the compressor 108 may be used. The separately installed compressor 108 may also be used. By high concentration pneumatic conveyance utilizing compressed air, the mixture is conveyed to the hopper 112 for a water-absorbing resin composition. During the route from the lift tank 106 to the hopper 112 for a water-absorbing resin composition, homogeneity of the mixture of water-absorbing resin particles (powder) and additive particles can dramatically be improved.

Pressure in the lift tank is not especially limited, however, preferably 0.1 to 10 MPa, more preferably 0.1 to 5 MPa, further preferably 0.1 to 1.0 MPa, and particularly preferably 0.1 to 0.5 MPa.

Pneumatic conveyance is largely classified into high concentration pneumatic conveyance and low concentration pneumatic conveyance, and usually, conveying pressure for high concentration pneumatic conveyance is set equal to or higher than 0.1 MPa, while conveying pressure for low concentration pneumatic conveyance is set below 0.1 MPa. High concentration pneumatic conveyance used in the present invention provides slower convey wind velocity, and requires smaller power than low concentration pneumatic conveyance. High concentration of powder conveyed in a conveying tube fills whole tube cross-section, plug-likely, by a powder group; in this case, because most of the particles do not collide with the wall surface of the conveying tube, tube wear or powder breakage is suppressed. In this way, powder is conveyed while filling the conveying tube plug-likely. In idealized plug conveyance, powder group and air are separated in an orderly manner to convey powder. However, it is rare that powder and air are separated in an orderly manner. In a practical system, an immovable deposition layer is formed at the bottom side of the tube, on which a plug moves by wave-like motion. In an alternative way, a deposition layer of powder grows from a hill-like cluster to a plug, and the plug, after going forward to a certain degree, collapses. By repeating these behaviors, powder is conveyed.

In the present invention, an apparatus, which attains high concentration pneumatic conveyance of such powder, is called a high concentration pneumatic conveyance apparatus. In other words, in high concentration pneumatic conveyance apparatus, powder moves in a conveying tube while forming a plug. Configuration of a high concentration pneumatic conveyance apparatus used in the present invention is not especially limited, however, it has at least a conveying tube in which a mixture of water-absorbing resin particles (powder) and additive particles moves.

Size of the apparatus is also not especially specified in the present invention, and may be determined in response to amount of a mixture to be conveyed, or conveying distance. Conveying distance of a mixture can be controlled by adjustment of the length of the conveying tube. In the present invention, the length of a conveying tube is preferably 1 to 200 m, more preferably 10 to 180 m, and further preferably 20 to 150 m. The length of the conveying tube value within such a range does not require excess apparatus cost, and is capable of producing a water-absorbing resin composition with high mixing homogeneity. In addition, a mixing state of a mixture can be controlled by adjusting the inner diameter of the conveying tube. The inner diameter of a conveying tube is preferably 5 to 100 mm, more preferably 10 to 100 mm, and further preferably 50 to 100 mm. According to one embodiment of the present invention, a water-absorbing resin composition is mixed at the same time as conveyance, however, a piping is not necessarily straight in consideration of only mixing, and may be loop-like or helix-like, and in addition, pneumatic transporting in the same piping may be repeated to improve mixing homogeneity.

Processing condition in high concentration pneumatic conveyance processing is also not especially limited. Processing time is preferably 0.1 to 20 minutes, more preferably 0.5 to 18 minutes and further preferably 1 to 15 minutes. Linear velocity at the end of the conveying tube is also not especially limited, however, preferably 0.1 to 50 m/sec, more preferably 0.5 to 45 m/sec, preferably 1 to 40 m/sec, and particularly preferably 4 to 30 m/sec. Solid-vapor ratio at the end of the conveying tube is also not especially limited, however, usually 10 to 200 kg-solid/kg-air, preferably 10 to 100 kg-solid/kg-air, more preferably 10 to 75 kg-solid/kg-air, and further preferably 10 to 50 kg-solid/kg-air. Processing amount of the mixture is not especially limited, however, preferably 1000 to 8000 kg/hr, more preferably 1300 to 7000 kg/hr, and further preferably 1500 to 6000 kg/hr.

High concentration pneumatic conveyance processing may be carried out either by a batch system or by a continuous system, however, preferably by a continuous system.

In addition, in the present embodiment, a mixture of water-absorbing resin particles (powder) and additive particles is conveyed using a high concentration pneumatic conveyance apparatus, and "particles (powder)" here represent wide concept including any embodiment to be conveyed using a high concentration pneumatic conveyance apparatus. As terms expressing embodiments generating in breaking a substance, various terms such as "powder", "cluster" and the like are used. "Particles (powder)" in the present invention should not be limited to any of theses terms, and represents all of the embodiments, which are fine in a degree to be conveyable using a high concentration pneumatic conveyance apparatus.

In the present invention, temperature of water-absorbing resin particles (powder) in a mixture supplied to the conveying tube is preferably over room temperature. In addition, water-absorbing resin particles (powder) are subjected to pneumatic transporting processing in a state of temperature under control within a range of more preferably 30 to 100° C., further preferably 40 to 95° C. and particularly preferably 45 to 95° C. A method for controlling water-absorbing resin particles (powder) within such a temperature range includes control by heating or cooling or keeping warm, as appropriate. In addition, low material temperature of water-absorbing resin particles (powder) may generate inhomogeneous mixing or cohesion. On the other hand, high material temperature of water-absorbing resin particles (powder) may cause deterioration or coloring of water-absorbing resin particles (powder), or require considerable energy for heating, and thus could energetically be disadvantageous. On the contrary, by maintaining temperature of water-absorbing resin particles (powder) supplied to the conveying tube, within the above temperature range, fluidity of particles (powder) is improved, and in addition, adhesion to the apparatus or clogging of a piping accompanying therewith is prevented, which is capable of attaining more homogeneous mixing, increased continuous operation capability and thus a water-absorbing resin composition excellent in various properties is obtained.

Temperature of water-absorbing resin particles (powder) supplied to the conveying tube can be determined by measurement of temperature of a mixture at the entrance of the conveying tube. "The entrance of the conveying tube" here represents the area around the place, where the mixture to be pneumatically conveyed enters the conveying tube. The upper limit of the temperature of water-absorbing resin particles (powder) is not especially limited, however, too high temperature setting could lower property as a water-absorbing resin, and in addition requires a large quantity of energy for maintaining temperature of particles (powder) at high temperature. From these viewpoints, temperature of water-absorbing resin particles (powder) in a mixture supplied to the conveying tube is preferably equal to or lower than 100° C.

Temperature of water-absorbing resin particles (powder) at the exit of the conveying tube is also preferably equal to or lower than 30° C., more preferably equal to or lower than 40° C. and further preferably equal to or lower than 50° C. "The exit of a conveying tube" here represents the area around the place, where the mixture is discharged from the conveying tube. By maintaining temperature of water-absorbing resin particles (powder) conveyed in the conveying tube at equal to or higher than predetermined value, reduction of property of a water-absorbing resin can be suppressed.

A method for controlling the temperature of water-absorbing resin particles (powder) at equal to or higher than 30° C. is not especially limited, and a method for installment of an external heating unit of the storing unit such as the hopper and the conveying tube, (for example, heating jacket, ribbon heater, electric heater, infrared ray lamp or the like) is preferably used. Specifically, by installment of a copper piping at the exterior wall of the first and the second hoppers (102, 104), along with the conveying tube 110, and by passing through steam inside the copper piping, temperature of water-absorbing resin particles (powder) supplied to the conveying tube 110, and water-absorbing resin particles (powder) moving inside the conveying tube 110 can be maintained at desired value.

A high concentration pneumatic conveyance apparatus itself may be produced using known technology. The high concentration pneumatic conveyance apparatus on the market may also be used. A heating unit, for maintaining a mixture in conveying at equal to or higher than predetermined temperature, may be installed at the high concentration pneumatic conveyance apparatus, if necessary.

Pneumatic transporting processing of a mixture of water-absorbing resin particles (powder) and additive particles, just in front of the product hopper, using the above high concentration pneumatic conveyance processing, is the most preferable embodiment, however, the processing may be carried out between any steps (polymerization step, drying step, surface processing step, and granulation step).

Mixing ratio between water-absorbing resin particles (powder) and additive particles, which are mixed in the present step, is not especially limited, and may be determined in consideration, as appropriate, of desired absorption characteristics and other characteristics of the resultant water-absorbing resin composition, and conventionally known knowledge. For example, mixing ratio (weight ratio) between water-absorbing resin particles (powder) and additive particles is preferably 100:0.01 to 100:1 (water-absorbing resin particles: additive particles), more preferably 100:0.1 to 100:0.7 (water-absorbing resin particles: additive particles), and further preferably 100:0.2 to 100:0.5 (water-absorbing resin particles: additive particles). The mixing ratio of the additive particles equal to or greater than 0.01 is preferable because caking index of the resultant water-absorbing resin composition is maintained at low value, and thus providing excellent fluidity in moisture absorption. On the other hand, the mixing ratio of the additive particles equal to or less than 1 is preferable because of providing excellent absorbency against pressure (AAP0.3) of the resultant water-absorbing resin composition. However, embodiments out side of these ranges may also be adopted naturally.

Explanation was given in detail above on the mixing step in the case where water-absorbing resin particles (powder) and additive particles are subjected to pneumatic transportation processing using an high concentration pneumatic conveyance apparatus, as an example, however, other mixing methods may also be used in execution of the first or the second embodiments of the present invention.

For example, as a mixer, any of a continuous or batch type mixer, or an airflow type mixer or a rotating stirring type mixer may be used, and in particular, use of a rotating stirring type mixer is preferable. As these mixers, a continuous or batch type mechanical mixer, for example, a conical blender, Nauta mixer, a kneader, a V-shaped mixer, a fluid bed type mixer, a turbulizer, a Rhedige mixer, a screw-type mixer, a ribbon blender, a mortar mixer and the like are included. Such a rotating stirring type mixer is rotated for mixing usually in 10 to 10000 rpm, and further 100 to 5000 rpm.

In addition, even in the case where mixing is carried out using these mixing methods, temperature of water-absorbing resin particles during mixing is preferably over room temperature. Water-absorbing resin particles (powder) are controlled within a temperature range of preferably 35 to 100° C., more preferably 40 to 95° C., and particularly preferably 45 to 90° C., and mixed with additive particles. A method for controlling water-absorbing resin particles (powder) at such temperature may include heating or heat-retention, as appropriate. Too low material temperature of water-absorbing resin particles (powder) may generate inhomogeneous mixing or cohesion. On the other hand, too high material temperature of water-absorbing resin particles (powder) may cause deterioration or coloring of water-absorbing resin particles (powder) and is energetically disadvantageous.

Furthermore, after mixing water-absorbing resin particles (powder) and additive particles, the resultant water-absorbing resin composition may be fed; this conveyance further accelerates mixing and provides a water-absorbing resin composition having higher-level property.

A conveying machine to be used is not especially limited as long as capable of continuous conveying, in addition to the above high concentration pneumatic conveyance apparatus, a screw conveyor, a spring conveyor, a belt conveyor, a bucket conveyor, and a vibration feeder or the like is included, and conveyance in a non-open state is preferable. Further more preferable one is a non-open type and that a feeder which has a vapor phase part inside a conveyor, that is, a receiving section of a resin or the like, partitioned by, for example, a partition plate or a screw or the like.

By installment of a rotary valve or the like at the discharge port along with the charging port, if necessary, of any of the above feeders, a non-open system can easily be attained without impairing continuous conveyance capability. One most easy in making non-open system is a pneumatic conveyer or a screw conveyor, in particular, a pneumatic conveyer. In addition, a pneumatic conveyer is a particularly excellent feeder, also in view of promoting effect of mixing between additive particles and water-absorbing resin particles (powder). In addition, a mixture is preferably heated or under heat-retention at the temperature above during conveyance, and for example, a heating system by a heating jacket, a ribbon heater, an electric heater, an infrared ray lamp or the like may be adopted.

Time required in mixing or conveyance is preferably equal to or shorter than 10 minutes (usually during 0.01 second to 10 minutes), more preferably during 0.1 second to 5 minutes, further preferably during 0.5 second to 3 minutes, particularly preferably during 1 second to 1 minute, and most preferably during 1 to 30 seconds. Too short time generally more likely provides insufficient mixing, while too long time provides a water-absorbing resin composition with deteriorated property caused by surface destruction. A conventional method was found to crush surface cross-linking caused by mixing of additives or crushing of cohesive substances, which thus lowered property of the resultant water-absorbing resin composition, however, the present invention is capable of attaining homogeneous mixing for a short period not conventionally attained, and thus providing a water-absorbing resin composition having high-level property.

(A Water-Absorbing Resin Composition)

According to the present invention, a water-absorbing resin composition made by mixing water-absorbing resin particles (powder) and additive particles is produced. A water-absorbing resin composition produced according to the present invention provides relatively less damage at the surface of water-absorbing resin particles (powder) as compared with a conventional mixing method. Therefore, the resultant water-absorbing resin composition is excellent in various properties. Preferable embodiments of properties of the resultant water-absorbing resin composition will be explained below, however, the scope of the present invention is by no means limited by the following embodiments.

Preferable embodiments of particle size (D50, logarithmic standard deviation (σζ) of the particle size distribution), bulk specific gravity, CRC, AAP0.3, caking index, fluid permeability, and PPUP of the resultant water-absorbing resin composition are the same as the above embodiments described as preferable embodiments of water-absorbing resin particles (powder); therefore, detailed explanation is omitted here.

Rate of water content of the resultant water-absorbing resin composition (specified by weight loss of 1 g of a composition at 180° C. for 3 hours) is preferably below 10% by weight, further preferably 0.1 to 7% by weight, and further preferably 0.2 to 5% by weight.

According to a production method of the present invention, reduction of various properties (for example, AAP0.3 or anti-caking characteristics) can dramatically be suppressed, during the change from water-absorbing resin particles (powder) before the mixing step, to a water-absorbing resin composition after the mixing step.

Specifically, retention rate of AAP0.3 of a water-absorbing resin composition after the mixing step relative to AAP0.3 of water-absorbing resin particles (powder) before the mixing step is preferably equal to or higher than 95%, more preferably equal to or higher than 96%, and further preferably equal to or higher than 97%. In addition, retention rate of AAP0.3 is calculated according to the following formula:

Retention rate(%) of AAP0.3=(AAP0.3 after mixing/ AAP0.3 before mixing)×100

Furthermore, the present inventors have intensively studied a factor generating property fluctuation in conventional absorbing goods, and have found that distribution of a water-absorbing resin in the absorbing goods became non-uniform, in the case of practically incorporating a water-absorbing resin, after shipping, into absorbing goods such as a diaper (for example, in preparation of absorbing goods by mixing a water-absorbing resin and pulp and the like); and also found out that in a water-absorbing resin composition obtained by a production method relevant to the first to the fourth embodiments of the present invention, the addition amount of additive particles or the amount of free additive particles satisfies a predetermined relation, and a composition satisfying this relation is capable of stably expressing high-level property.

Namely, the fifth embodiment of the present invention provides a water-absorbing resin composition containing 100 parts by weight of water-absorbing resin particles and 0.01 to 1 part by weight of additive particles, characterized in that percent by weight of the additive particles, (X [%]), based on 100% by weight of the water-absorbing resin particles in the composition, and weight ratio of free additive particles, (Y), relative to the percent by weight, (X [%]), satisfy the following formula:

$$0.04(x)^{0.1} \leq y \leq 0.2(x)^{0.5}$$

In the present embodiment, X represents percent by weight of the above additive particles relative to 100 parts by weight of the above water-absorbing resin particles in a composition; namely, in the case where the water-absorbing resin composition contains 100 parts by weight of the water-absorbing resin particles and 0.3 part by weight of the additive particles, then X is 0.3 [%].

In addition, in the present embodiment, Y represents weight ratio of free additive particles. "Free additive particles" here represents percent by weight of the additive particles contained in suspended solids derived from a water-absorbing resin composition, under predetermined condition, based on 100% by weight of a water-absorbing resin in a composition, expressed as a ratio in comparison with the above X. Here, as value of X or Y, value obtained by a method described in Examples to be referred to below should be adopted.

In the present embodiment, the above X and the above Y satisfy the following formula:

$$0.04(X)^{0.1} \leq Y \leq 0.2(X)^{0.5}$$

Here, Y larger than the upper limit shows the additive particles are in a state of being easy to leave from the composition. In this case, since it is difficult for the additive particles to exert their effect, it is easy for caking index to increase. On the other hand, Y smaller than the lower limit shows the additive particles are dispersed so finely as to enter fine voids on the surface of the water-absorbing resin particles. In this case, although it is not easy for the additive particles to leave, original function of the additive particles to suppress adhesion between the water-absorbing resin particles lowers, and therefore, it is easy for caking index to increase. In other words, by controlling the Y so that the above-described formula is satisfied, handling property of the water-absorbing resin composition in a high-humidity environment is improved and an absorbing goods incorporating the composition exerts desired properties.

In the present invention, X and Y preferably satisfy the following formula:

$$0.08(X)^{0.35} \leq Y \leq 0.19(X)^{0.5}$$

and more preferably satisfy the following formula:

$$0.13(X)^{0.5} \leq Y \leq 0.185(X)^{0.5}$$

Here, X is preferably 0.01 to 1, more preferably 0.1 to 0.7, and further preferably 0.2 to 0.5 in response to the above-described preferred mixing ratio (weight ratio) between the water-absorbing resin particles and the additive particles. The X equal to or larger than 0.01 lowers caking index, and the X equal to or smaller than 1 suppresses the lowering of absorbency against pressure (AAP0.3).

The resultant water-absorbing resin composition obtained by a production method of the present invention is one which absorbs not only water but also various fluids containing water, such as body fluid, as a line solution, urine, blood, water in cement, water contained in fertile or the like, and suitably be used in various industrial fields including hygienic goods such as a paper diaper or a sanitary napkin, so-called an incontinence pad and the like, civil engineering, agriculture and gardening and the like.

Furthermore, the resultant water-absorbing resin composition obtained by a production method of the present invention is capable of exerting new function by containing a deodorant, an antibacterial agent, perfume, drug, a plant growth co-agent, a fungicide, a foaming agent, pigment, dye, a hydrophilic short fiber, fertile, or the like, in an amount of preferably 0 to 30% by weight, more preferably 0.001 to 15% by weight relative to total amount of the composition.

EXAMPLES

The present invention will be explained in more detail using Examples, however, the scope of the present invention is by no means limited only to the following Examples. In addition, "%" described in Examples and Comparative Examples below represents "% by weight" unless otherwise specified. Measurement methods and evaluation methods for various parameters in Examples and Comparative Examples will be shown below.

(A) Measurement of Rate of Content [%] of Over Cohesive Particles in Additive Particles Under condition of a temperature of 23° C. and a humidity of 50% RH, 50.0 g of additive particles are charged onto a JIS standard sieve, Z8801-1, with a mesh opening of 1000 μm (made of stainless steel: inner diameter=200 mm, depth=45 mm), and then subjected to classification for 5 minutes using a Ro-Tap type sieving vibrator for 200ϕ (manufactured by IIDA SEISAKUSHO Co., Ltd.: number of vibration=290 r/m, number of hammer=165 r/m, 100 V, 60 Hz) to measure weight of the additive particles left on the sieve with a mesh opening of 1000 μm, and this amount was assumed as W3 (g). Then, rate of content [%] of over cohesive particles in the additive particles is calculated in accordance with the following formula:

$$\text{Rate of content[\%] of over cohesive particles} = (W3/50) \times 100$$

(B) Measurement of % by Weight (X [%]) of Additive Particles in a Composition

Because silica fine particles, which are cohesive fine particles, were used as the additive particles in the present Example, a measurement method for % by weight (X) of the additive particles is explained here on the case where the additive particles are the silica fine particles, as an example, however, even in the case where other material is used as the additive particles, % by weight (X) of the additive particles can be determined by a similar method.

(1) Preparation of a Calibration Curve

Standard samples are prepared by addition and mixing each of 0, 0.15, 0.3, 0.5 and 1.0% by weight of silica fine particles (Aerosil 200, manufactured by Japan Aerosil Co. Ltd.) relative to 100% by weight of a water-absorbing resin not added with additive particles (for example, a water-absorbing resin (iii) in Reference Example to be described later).

Subsequently, a calibration curve is prepared by determination of absorbance (wavelength: 410 nm) on these standard samples with known concentrations of silica fine particles.

(2) Measurement of % by Weight (X) of Additive Particles (Silica Fine Particles) in a Composition 1) Into a 250-ml polypropylene (PP) beaker, 0.500 g of a test sample is added, and 0.5 g of anhydrous sodium carbonate is further added.

2) Into the above mixture 1), 100 ml of deionized water (grade 3, ISO3696) at 80° C. is added using a 100 ml PP measuring cylinder, and a 2.5 cm stirrer chip is put in and stirred the solution for 2 hours on a magnetic stirrer while keeping at 80° C. to dissolve solid silica.

3) The resulting solution 2) is filtered using a gather folded quantitative filter (No. 5C (185 mm), manufactured by Toyo Roshi Kaisha, Ltd.) and a PP funnel, and the filtrate is received in a 100-ml PP measuring flask.

4) At the timing when there is no liquid left on the filter present in the PP funnel (after about 1 hour), 3 ml of 6N hydrochloric acid is added using a PP Komagome pipet to shrink gel as well as possible.

5) Into the resultant filtrate, 3 ml of 6N hydrochloric acid, subsequently 4 ml of 5% ammonium molybdate solution are added twice, then, deionized water is added to make 100 ml, and sealed to sufficiently shake.

6) The resultant colored solution of 5) is subjected to determination of absorbance (ABS) using a 10-mm cell at a wavelength of 410 nm, within 5 to 20 minutes after coloring, by a spectrometer (IU-1100 spectrometer, manufactured by Hitachi Ltd.). Similar procedure is taken using only deionized water, as a blank.

7) Value obtained by subtracting blank value from the absorbance determined is adopted as absorbance of a test sample, to determine % by weight (X [% by weight]) of silica fine particles in the test sample, based on the calibration curve prepared above.

(C) Measurement of Weight Ratio (Y) of Free Additive Particles

Weight ratio (Y) of free additive particles can be determined, by firstly measuring weight ratio of suspended solids occupying in total weight of the water-absorbing resin composition, and then, weight ratio of the additive particles occupying in total weight of the suspended solids. In addition, explanation is given here also in the case where the additive particles are the silica fine particles, as an example, however, even in the case where other material is used as the additive particles, weight ratio (Y) of the free additive particles can be obtained by a similar method above.

(1) Measurement of Weight Ratio (A [%]) of the Suspended Solids Occupying in Total Weight of the Water-Absorbing Resin Composition Amount of the suspended solids from the water-absorbing resin composition is measured using "Heubach Dustmeter 2000" manufactured by Seishin Enterprise Co., Ltd, under the following measurement conditions:

Work environment: 18 to 22° C./45 to 55 RH %
Sample: 100.00 g
Model: Type (I) (horizontal type)
Rotation: 30 R/min.
Airflow: 20.0 L/min
Time: 60 min (because upper limit setting is 30 min, twice runs of 30 min)
Collecting filter: Paper filter (GC90 manufactured by ADVANTEC MFS, Inc.)

Weight increase [mg] of the filter after 60 minutes from start of the measurement is measured to calculate weight ratio (A [%]) of the suspended solids occupying in total weight of the water-absorbing resin composition, according to the following formula:

$$A[\%] = (\text{weight increase of the filter after 60 minutes from start of the measurement})/1000$$

(2) Measurement of weight ratio (B [%]) of the additive particles occupying in total weight of the suspended solids Weight ratio (B [%]) of the additive particles can be calculated based on each of measured % by weight values of a Na element and a Si element contained in the suspended solids, along with neutralization rate of the water-absorbing resin (in the case where a neutralized salt is a Na salt) and average molecular weight thereof.

Specifically, suitable amount of the suspended solids are sampled from the filter used in the measurement of weight ratio (A) of the suspended solids in the above (C) (1), and then moved on a sample holder for SEM, adhered with a 5 mm×5 mm carbon tape. In this case, the suspended solids are uniformly spread on the carbon tape. The suspended solids are subjected to quantitative analysis by the ZAF method using SEM-EDS (Energy Dispersion X-ray Spectrometer). In this way, weight ratio of the Na element (Na %) and weight ratio of the Si element (Si %) occupying in total weight of the suspended solids can be measured. Measurement conditions using the SEM-EDS are as follows:

Measurement Conditions:
Apparatus: Scanning electron microscope (JSM-5410LV, SCANNING MICROSCOPE, manufactured by JOEL Co., Ltd.)
Acceleration voltage: 20 kV
Magnification: 50 times
Measurement view: about 900 μm×1200 μm, in a state of at least 50% of the measurement view area is covered with the suspended solids
Si peak: SiK 1.739 keV
Na peak: NaK 1.041 keV In the case where peaks originated from other elements (for example, NaK, ZnLa and the like) overlapping these peaks, are present, these other peaks are subtracted for compensation.

In addition, neutralization rate (N [% by mol]) and average molecular weight (Mw) of the water-absorbing resin can be measured by the following methods:

Firstly, 184.3 g of 0.90% by weight aqueous saline solution is weighed into a 250-ml plastic container equipped with a cap, and 1.00 g of the water-absorbing resin particles or a water-absorbing agent is added into the aqueous solution; stirring is performed for 1 hour by rotation of a stirrer to extract soluble components in the resin.

The resultant extracted solution is subjected to filtering using a sheet of filter paper (trade name: JIS P3801, No. 2, manufactured by ADVANTEC TOYO MFS, Inc., with a thickness of 0.26 mm, and a retaining particle diameter of 5 μm), and 50.0 g of the filtrate is weighed as a measurement solution.

Firstly, by using only a 0.90% by weight aqueous saline solution, titration is performed using an aqueous solution of 0.1 N NaOH, till a pH of 10; subsequently by titration using an aqueous solution of 0.1 N HCl, till a pH of 2.7, blank titration amounts ([bNaOH] ml, [bHCl] ml) are obtained.

By similar titration operation on the measurement solution, titration amounts ([NaOH] ml, [HCl] ml) are obtained.

Based on the titration amounts obtained by the above operation, neutralization rate (N [% by mol]) and average molecular weight (Mw) of the water-absorbing resin or the water-absorbing agent are calculated according to the following formulae:

$$N[mol\%]=(1-([NaOH]-[bNaOH])/([HCl]-[bHCl]))\times 100$$

$$Mw=72.06\times(1-N/100)+94.05\times N/100$$

From the Na % and Si % values, along with the neutralization rate (N [% by mol]) and average molecular weight (Mw) of the water-absorbing resin measured above, weight ratio (B [%]) of the additive particles occupying in total weight of the suspended solids can be calculated, according to the following formula:

Weight ratio($B[\%]$) of the additive particles occupying in total weight of the suspended solids=(Si %/28.08)×60.08/((Si %/28.08)×60.08+(Na %/2)/(N/100)×$Mw$)×100

In addition, in the above explanation, explanation was given on the case where the neutralized salt of the water-absorbing resin is a Na salt, as an example, however, B can be calculated as well, in accordance with the present method, even in the case where other salts are used as the neutralized salts of the water-absorbing resin; for example, in the case where the neutralized salt of the water-absorbing resin is a potassium salt, instead of the Na % and Si % values, weight ratio (K %) of a K element occupying in total weight of the suspended solids, and Si % values may be adopted.

In addition, weight ratio of the additive particles in the suspended solids is preferably measured in accordance with the above method, however, in the case where components are unknown, or other elements are included in large amounts; other known measurement methods such as element analysis and the like may be adopted, as long as accurate value is obtainable.

(3) Measurement of Weight Ratio (C [%]) of the Free Additive Particles Occupying in Total Weight of the Water-Absorbing Resin Composition Weight ratio (C [%]) of the free additive particles occupying in total weight of the water-absorbing resin composition is calculated according to the following formula:

$$C[\%]=A\times B/100$$

(4) Measurement of Weight Ratio (Y) of the Free Additive Particles

Finally, weight ratio (Y) of the free additive particles is calculated according to the following formula:

$$Y=C[\%]/X[\%]$$

(D) Measurement of Weight of Foreign Matters

Two kg of the water-absorbing resin composition, which passed through a 1000 μm mesh (preferably passed through a 850 μm mesh) is randomly sampled and subjected to processing by a vibration shaker (model DY-300, manufactured by Miyako Bussan Co., Ltd., and a screen mesh having a mesh opening of 1.0 mm, inner diameter of 300 mm, and depth of 120 mm, manufactured by IIDA SEISAKUSHO Co., Ltd) at a speed of about 2 kg/min; number of foreign matters left on the sieve is counted. The above procedure is repeated 5 times, and count numbers are averaged to obtain amount of foreign matters [particles/kg] of the measurement sample. In addition, in the case where direct counting of foreign matters is difficult on the sieve, counting may be performed after transferring them onto a sheet of easy distinguishable color (such as black color).

(E) Measurement of Centrifuge Retention Capacity (CRC) to an Aqueous Solution of Sodium Chloride of 0.90% by Weight Into a bag (60 mm×85 mm) made of non-woven fabric, 0.20 g of a water-absorbing resin or a water-absorbing resin composition is uniformly charged. Then this bag is immersed into a saline solution (an aqueous solution of sodium chloride of 0.90% by weight) adjusted at 25° C.±2° C. After 30 minutes, the bag is pulled up and subjected to drainage using a centrifugal separator (Type H-122, a compact type centrifugal separator manufactured by KOKUSAN Co., Ltd.) at 250 G (250×9.81 m/s$^2$) for 3 minutes to measure bag weight, W4 (g). In addition, the same procedure is carried out without using the water-absorbing resin or the water-absorbing resin composition to measure bag weight at this time, W5 (g). Then, using these weights (W4 and W5), centrifuge retention capacity (CRC [g/g]) is calculated according to the following formula:

$$CRC[g/g]=\{(W4-W5)/(\text{weight of the water-absorbing resin (composition)})\}-1$$

(F) Measurement of Absorbency Against Pressure (AAP0.3)

On a 400-mesh stainless steel mesh screen (a mesh opening of 38 μm), which is welded at one side (bottom) of the cross-sections of a plastic supporting cylinder having an inner diameter of 60 mm, 0.900 g of the water-absorbing resin or the water-absorbing resin composition (hereafter may be referred to simply as "water-absorbing resin/water-absorbing resin composition") is uniformly spread; a piston is placed thereon, having an exterior diameter of a little smaller than 60 mm, so as not to generate space between the supporting cylinder and the wall surface thereof, and not to inhibit up and down motion; to measure total weight of the supporting cylinder, the water-absorbing resin/water-absorbing resin composition, and the piston, as W6 (g).

On this piston, a load is applied, so that a load of 1.9 kPa (about 20 g/cm², about 0.3 psi) including the piston itself can be applied onto the water-absorbing resin/a water-absorbing resin composition, to complete a set of a measurement apparatus. At the inside of a petri dish with a diameter of 150 mm, a glass filter with a diameter of 90 mm and a thickness of 5 mm is placed, and a saline solution (an aqueous solution of sodium chloride of 0.90% by weight) adjusted at 25° C.±2° C., is added so as to be the same level as the top surface of the glass filter; on this solution, a sheet of a filer paper with a diameter of 9 cm (No. 2 manufactured by Toyo Roshi Kaisha, Ltd.) is placed, so that both surfaces thereof are wet; and excess solution is removed.

The whole set of the measurement apparatus is placed on thus wetted filter and the solution is subjected to absorption under load. Upon lowering of the liquid surface level below the top part of the glass filter, the solution is further added so as to maintain the liquid surface level constant. After 1 hour, the whole set of the measurement apparatus is lifted up, and weight excluding the load (total weight of the supporting cylinder, the swollen water-absorbing resin/water-absorbing resin composition, and the piston) is measured again, as W7 (g). Then, AAP0.3 [g/g] is calculated from these weights (W6 and W97) according to the following formula:

AAP0.3 $[g/g]=(W7-W6)/$(weight of the water-absorbing resin/weight of water-absorbing resin composition)

(G) Measurement of Caking Index

On the bottom of a plastic cup with a diameter of the bottom surface of 50 mm, and a height of 11 mm, 2.00 g of the water-absorbing resin or the water-absorbing resin composition, which passed through a 850 μm mesh, is uniformly spread, and then quickly charged into a chamber with constant temperature and humidity (PLATIOOUS LUCIFER PL-2G, manufactured by Tabai Espec Corp.) adjusted, in advance, at a temperature of 25° C. and a relative humidity of 90% RH, and is subjected to standing still for 1 hour or 5 hours. After that, the water-absorbing resin or the water-absorbing resin composition thus moisture absorbed is transferred onto a JIS standard sieve with a diameter of 7.5 cm and a mesh opening of 2000 μm, and then subjected to sieving for 5 minutes using a Ro-Tap type sieving vibrator (IIDA SIEVE SHAKER, TYPE:ES-65 model, SER. No. 0501, manufactured by IIDA SEISAKUSHO Co., Ltd) to measure weight of the water-absorbing resin or the water-absorbing resin composition left on the sieve, and weight of the water-absorbing resin or the water-absorbing resin composition passed through the sieve, as W8 (g) and W9 (g), respectively. Caking index is calculated from these weights (W8 and W9) according to the following formula. In addition, an average value from 5 measurements is adopted as the caking index, and lower caking index indicates more excellent fluidity in moisture absorption.

Caking index $[\%]=[W8/(W8+W9)]\times 100$

Reference Example

In a kneader equipped with 2Σ type blades, an aqueous monomer solution was prepared, composed of sodium acrylate, acrylic acid and water, with a monomer concentration of 40% by weight, and a neutralization rate of 75% by mol. Into this monomer solution, polyethylene glycol diacrylate (average ethylene glycol unit number: 9) is dissolved as an internal surface cross-linking agent, so as to be 0.03% by mol (relative to the monomers).

Then, into the above aqueous monomer solution, nitrogen gas was blown to reduce dissolved oxygen in the aqueous monomer solution, and whole of the inside of a reactor was substituted with nitrogen. Subsequently, after adjusting temperature of the aqueous monomer solution at 22° C. while rotating the 2Σ type blades, 0.12 g/mol (relative to the monomers) of sodium persulfate, and 0.005 g/mol (relative to the monomers) of L-ascorbic acid were added, as polymerization initiators.

Because the monomer aqueous solution turned turbid just after initiation of polymerization, rotation of the blades were stopped. After polymerization temperature reached 50° C., the blades were rotated again to continue polymerization in a kneader under stirring to yield, after about 50 minutes, a water-containing gel-like cross-linked polymer with weight average particle diameter of about 2 mm.

The resultant water-containing gel-like cross-linked polymer was dried at 170° C. for about 60 minutes using a hot air dryer. Subsequently, the dried substance was crushed by a roll mill crusher and classified using sieves having a mesh opening of 850 μm and 150 μm (for removing the portions over and below the sieves), to yield a particle-like base polymer (i) having a rate of water content of 3% by weight, and a weight average particle diameter of 310 μm. The resultant particle-like base polymer (i) did not substantially contain particles with a particle diameter of equal to or larger than 850 μm, and content of fine particles with a particle diameter of smaller than 150 μm was 4% by weight.

100 parts by weight of the resultant particle-like base polymer (i) above, and 2.84 parts by weight of a surface cross-linking agent composed of 1,4-butane diol:propylene glycol:water=0.24:0.4:2.2 (weight ratio), were spray mixed under stirring using a continuous high-speed stirring mixer (trade name: turbulizer, manufactured by Hosokawa Micron Group).

A mixture of the particle-like base polymer (i) and the surface cross-linking agent was subjected to continuous heating processing using a twin screw stirring dryer (trade name: paddle drier, manufactured by Nara Machinery Co., Ltd.) adjusted to have a surface temperature of 190° C. by charging heated steam into the inner wall, stirring disk and rotation axis: average residence time was 60 minutes. Subsequently, the mixture was cooled using a twin screw stirring drier where water of 35° C. flows into the inner wall, stirring disk and rotation axis (an average residence time of 30 minutes), to yield surface cross-linked water-absorbing resin particles (ii).

Subsequently, the water-absorbing resin particles (ii) were subjected to passing through a particle size controller (trade name: flash mill, manufactured by Fuji Paudal Co., Ltd.) and passing through a sieve with a screen mesh opening of 850 μm to yield water-absorbing resin particles (iii) having an indeterminate form. In addition, measurement results of properties of the water-absorbing resin particles (iii) were as follows: CRC=35 [g/g], AAP0.3=32 [g/g], D50=330 [μm], σζ=0.35, bulk specific gravity=0.64, SFC=3×10⁻⁷ [cm³×sec/g], PPUP=33[%], rate of water content=3 [%], and caking index=100 [%].

Example 1

Water-insoluble cohesive silica fine particles (trade name: Aerosil 200, manufactured by Japan Aerosil Co. Ltd.: primary particle diameter: about 12 nm, BET specific surface area: about 200 m²/g, drying loss: equal to or less than 1% by weight), as additive particles, were crushed so that content of over cohesive particles is 0%. The crushing of the silica fine particles was performed at the same time as conveying (filling) of silica from a container bag to a hopper, by an aired pump (an air drive type diaphragm pump). Specifically, the crushing was performed by installing a screen mesh (mesh opening: 1410 μm) at a conveying tube for filling, and subjecting the silica fine particles to pass through the screen mesh.

The silica fine particles crushed in this way were added in an amount of 0.3 part by weight relative to 100 parts by weight of the water-absorbing resin particles (iii) obtained in the above Reference Example; the mixture was conveyed to a product hopper by pneumatic conveying under a pressure condition of 0.095 MPa, and then packed in a bag to prepare a water-absorbing resin composition (1). On the water-absorbing resin composition (1), various parameters were measured; the specifications and measurement results in this Example are shown in Table 2 and 3.

Example 2

A water-absorbing resin composition (2) was obtained by a same method as in the above Example 1, except that the addition amount of the silica fine particles was changed to 0.5 part by weight. On the water-absorbing resin composition (2), various parameters were measured; the specifications and measurement results in this Example are shown in Table 2 and 3.

Example 3

A water-absorbing resin composition (3) was obtained by a same method as in the above Example 1, except that the addition amount of the silica fine particles was changed to 0.15 part by weight. On the water-absorbing resin composition (3), various parameters were measured; the specifications and measurement results in this Example are shown in Table 2 and 3.

Example 4

A water-absorbing resin composition (4) was obtained by a same method as in the above Example 1, except that instead of using the silica fine particles (Aerosil 200), a lot having low over cohesive particles was selected among silica fine particles (trade name: Aerosil 200 CF, manufactured by Japan Aerosil Co. Ltd.: primary particle diameter: about 12 nm, BET specific surface area: about 200 m$^2$/g, drying loss: equal to or less than 1% by weight) and used without crushing. On the water-absorbing resin composition (4), various parameters were measured; the specifications and measurement results in this Example are shown in Table 2 and 3.

Example 5

A water-absorbing resin composition (5) was obtained by a same method as in the above Example 1, except that instead of using the silica fine particles (Aerosil 200), silica fine particles (the above Aerosil 200 CF) were used. On the water-absorbing resin composition (5), various parameters were measured; the specifications and measurement results in this Example are shown in Table 2 and 3.

Example 6

A water-absorbing resin composition (6) was obtained by a same method as in the above Example 1, except that crushing of over cohesive particles was performed using a jet mill (manufactured by Hosokawa Micron Group). On the water-absorbing resin composition (6), various parameters were measured; the specifications and measurement results in this Example are shown in Table 2 and 3.

Comparative Example 1

A comparative water-absorbing resin composition (1) was obtained by a same method as in the above Example 1, except the silica fine particles (Aerosil 200) were used as they are. On the comparative water-absorbing resin composition (1), various parameters were measured; the specifications and measurement results in this Comparative Example are shown in Table 2 and 3.

Comparative Example 2

A comparative water-absorbing resin composition (2) was obtained by a same method as in the above Comparative Example 1, except the addition amount of the silica fine particles was set to be 0.5 part by weight. On the comparative water-absorbing resin composition (2), various parameters were measured; the specifications and measurement results in this Comparative Example are shown in Table 2 and 3.

Comparative Example 3

Relative to 100 parts by weight of the resultant water-absorbing resin particles (iii) in the above Reference Example, 0.3 part by weight of silica fine particles (Aerosil 200) were added as additive particles, and mixed for 60 minutes using a mixer (trade name: Plough Share mixer, Pacific Machinery & Engineering Co., Ltd.) under condition of a rotation number of a main blade of 60 rpm, and a rotation number of a chopper of 100 rpm. Subsequently, the resultant mixture was conveyed to a product hopper by pneumatic conveying under a pressure condition of 0.095 MPa, and then packed in a bag to prepare a comparative water-absorbing resin composition (3). On the comparative water-absorbing resin composition (3), various parameters were measured; the specifications and measurement results in this Comparative Example are shown in Table 2 and 3.

Comparative Example 4

A comparative water-absorbing resin composition (4) was obtained by a same method as in the above Comparative Example 3, except that the mixing time in the mixer (Plough Share mixer) was set to 1 minute. On the comparative water-absorbing resin composition (4), various parameters were measured; the specifications and measurement results in this Comparative Example are shown in Table 2 and 3.

Comparative Example 5

Relative to 100 parts by weight of the resultant water-absorbing resin particles (ii) in the above Reference Example, 10 parts by weight (reduced value as solid content: 0.3% by weight) of 3% by weight of aqueous solution of colloidal silica (PL-1, manufactured by FUSO CHEMICAL CO., LTD.; primary particle diameter: 15 nm) as additive particles was added. Subsequently, the resultant mixture was subjected to hardening at 60° C. for 60 minutes, and to passing a particle size controller and passing through a sieve having a mesh opening of 850 μm. Subsequently, the resultant mixture was conveyed to the product hopper by pneumatic conveying under a pressure condition of 0.095 MPa, and then packed in a bag to prepare a comparative water-absorbing resin composition (5). On the comparative water-absorbing resin composition (5), various parameters were measured; the specifications and measurement results in this Comparative Example are shown in Table 2 and 3.

Example 7

Water-insoluble cohesive silica fine particles (trade name: Aerosil 200, manufactured by Japan Aerosil Co. Ltd.: primary particle diameter: about 12 nm, BET specific surface area: about 200 m$^2$/g, drying loss: equal to or less than 1% by weight, ratio of cohesive particles with cohesive particle diameter of below 53 μm: 10%, apparent bulk specific gravity: 0.05 g/cm$^3$, content of over cohesive particles: 40% by weight), were prepared as additive particles.

The resultant water-absorbing resin particles (iii) in the above Reference Example were charged in the first hopper 102 of a high concentration pneumatic conveying apparatus, shown in FIG. 1, and the silica fine particles prepared above were charged into the second hopper 104.

Subsequently, the water-absorbing resin particles (iii) and the silica fine particles were mixed by high concentration pneumatic conveying processing using the high concentration pneumatic conveying apparatus, shown in FIG. 1; size of the high concentration pneumatic conveying apparatus, and processing conditions of the conveying processing were as follows: mixing ratio (weight ratio): 100:0.3 (water-absorbing resin (ii): silica fine particles), lift tank pressure: 0.21 MPa, length of the conveying tube: 30 m, inner diameter of the conveying tube: 55 mm, processing time: 1.5 minutes, linear velocity at the end of the conveying tube: 5.6 m/sec, solid-air ratio at the end of the conveying tube: 43.8 kg-solid/kg-air, processing amount of the mixture: 1300 kg/hr, temperature of the mixture at the entrance of the conveying tube: 35° C., and temperature of the mixture at the exit of the conveying tube: 32° C. Processing conditions in the present Example are shown in Table 3.

In addition, a mixing unit was not especially installed in the lift tank. A sample conveyed by pneumatic conveying to a hopper of a water-absorbing resin composition, and further packed in a bag was used as a water-absorbing resin composition (7). On the water-absorbing resin composition (7), various parameters were measured; the specifications and measurement results in this Example are shown in Table 2 and 3.

Comparative Example 6

A comparative water-absorbing resin composition (6) was obtained by a same method as in the above Example 7, except that a bucket conveyor (manufactured by Makino Mfg. Co., Ltd.) was used as a mixing unit for mixing the water-absorbing resin particles (iii) and the silica fine particles, instead of the high concentration pneumatic conveying apparatus, shown in FIG. 1. On the comparative water-absorbing resin composition (6), various parameters were measured; the specifications and measurement results in this Comparative Example are shown in Table 2 and 3.

Comparative Example 7

A comparative water-absorbing resin composition (7) was obtained by a same method as in the above Comparative Example 6, except that a Plough Share mixer (manufactured by Pacific Machinery & Engineering Co., Ltd., a rotation number of a main blade of 250 rpm, a rotation number of a chopper of 1800 rpm, and a mixing time of 60 minutes) was installed as a mixing unit for mixing the water-absorbing resin particles (iii) and the silica fine particles, before supplying to the bucket conveyor. On the comparative water-absorbing resin composition (7), various parameters were measured; the specifications and measurement results in this Comparative Example are shown in Table 2 and 3.

Comparative Example 8

A comparative water-absorbing resin composition (8) was obtained by a same method as in the above Example 7, except, that low concentration conveying was performed under pneumatic conveying condition of a lift tank pressure of 0.05 MPa, a linear velocity at the end of 8 m/sec, and a solid-air ratio at the end of 8 kg-solid/kg-air. Processing conditions in the present Comparative Example are shown in Table 3. On the comparative water-absorbing resin composition (8), various parameters were measured; the specifications and measurement results in this Comparative Example are shown in Table 2 and 3.

Example 8

A water-absorbing resin composition (8) was obtained by a same method as in the above Example 1, except that pressure condition of the pneumatic conveying was set to be 0.21 MPa. On the water-absorbing resin composition (8), various parameters were measured; the specifications and measurement results in this Example are shown in Table 2 and 3.

Example 9

A water-absorbing resin composition (9) was obtained by a same method as in the above Example 1, except that instead of using the silica fine particles (Aerosil 200), silica fine particles (trade name: Aerosil 300, manufactured by Japan. Aerosil Co. Ltd.: primary particle diameter: about 7 nm, BET specific surface area: about 300 m$^2$/g, drying loss: equal to or less than 2% by weight) was used. On the water-absorbing resin composition (9), various parameters were measured; the specifications and measurement results in this Example are shown in Table 2 and 3.

Example 10

A water-absorbing resin composition (10) was obtained by a same method as in the above Example 1, except that instead of using the silica fine particles (Aerosil 200), silica fine particles (trade name: Aerosil 380, manufactured by Japan Aerosil Co. Ltd.: primary particle diameter: about 7 nm, BET specific surface area: about 380 m$^2$/g, drying loss: equal to or less than 2.5% by weight) was used. On the water-absorbing resin composition (10), various parameters were measured; the specifications and measurement results in this Example are shown in Table 2 and 3.

Example 11

Relative to 100 parts by weight of the resultant water-absorbing resin particles (iii) in the above Reference Example, 0.3 part by weight of silica fine particles (Aerosil 200) were added as additive particles, and mixed for 1 minute using a mixer (trade name: Plough Share mixer, Pacific Machinery & Engineering Co., Ltd.) under condition of a rotation number of a main blade of 60 rpm, and a rotation number of a chopper of 100 rpm. Subsequently, the resultant mixture was further mixed using a bucket conveyer (manufactured by Makino Mfg. Co., Ltd.), and then packed in a bag to prepare a water-absorbing resin composition (11). On the water-absorbing resin composition (11), various parameters were measured; the specifications and measurement results in this Example are shown in Table 2 and 3.

Example 12

Using a mixer, 65 parts by weight of the water-absorbing resin composition (6) obtained in the above Example 6, and 35 parts by weight of wood pulp were mixed in an environment of a temperature at 25° C. and a relative humidity of 90%. By subjection the resultant mixture to airlaid web-making using a batch type airlaid web-making machine, a web with a size of 120 mm×400 mm was formed on a wire screen formed in 400 mesh size (mesh opening of 38 μm). Further, by pressing this web under a pressure of 2 kg/cm² for 5 seconds, absorbing goods having a basic weight of about 0.047 g/cm² (weight ratio of the water-absorbing resin composition occupying in the absorbing goods was 65% by weight) was obtained.

Subsequently, a back sheet (a fluid impermeable sheet) made of fluid impermeable polypropylene and having what is called leg-gathering, the above absorbing goods, and a top sheet made of fluid permeable polypropylene (a fluid permeable sheet) were adhered each other in this order, using a double-faced adhesive tape, and two, what is called, tape fasteners were provided thereon to obtain absorbing goods (diaper). The absorbing goods was attached on, what is called, a Kewpie doll (a body length of 55 cm, and a weight of 5 kg); after laying the doll on its stomach, a tube was inserted between the absorbing goods and the doll to four times repeatedly inject a 0.9% by weight aqueous sodium chloride solution, 50 g each time, at the section for discharging urine in a human body, in 20 minutes interval. The result shows no leakage of the aqueous sodium chloride solution from the absorbing goods, and uniform swelling of an absorbing substance in the absorbing goods.

Comparative Example 9

A comparative absorbing goods was obtained similarly as in the above Example 12, except that instead of the water-absorbing resin composition (6), the comparative water-absorbing resin composition (1) obtained in the above Comparative Example 1 was used. Using the comparative absorbing goods, similar evaluation was performed; this time, at the fourth injection of the aqueous sodium chloride solution, leakage of the aqueous sodium chloride solution was found from the absorbing goods. In addition, an absorbing substance in the absorbing goods was observed to be localized, and in a non-uniform state in view of swollen state portion and not so swollen state portion.

TABLE 1

| | Additive kind | Mixer | Conveying type | Form of conveying | Pressure in pressurization tank (MPa) | Over cohesive particles content (%) | Addition amount (X) (%) | Weight ratio of free additive particles (%) | 0.04 (x)0.1 ≤ y ≤ 0.2 (x)0.5 |
|---|---|---|---|---|---|---|---|---|---|
| Example 1 | Aerosil 200 | — | pneumatic conveying | — | 0.095 | 0 | 0.3 | 0.10 | YES |
| Example 2 | Aerosil 200 | — | pneumatic conveying | — | 0.095 | 0 | 0.5 | 0.12 | YES |
| Example 3 | Aerosil 200 | — | pneumatic conveying | — | 0.095 | 0 | 0.15 | 0.07 | YES |
| Example 4 | Aerosil 200CF | — | pneumatic conveying | — | 0.095 | 15 | 0.3 | 0.10 | YES |
| Example 5 | Aerosil 200CF | — | pneumatic conveying | — | 0.095 | 0 | 0.3 | 0.10 | YES |
| Example 6 | Aerosil 200 | — | pneumatic conveying | — | 0.095 | 0 | 0.3 | 0.10 | YES |
| Comp. Ex. 1 | Aerosil 200 | — | pneumatic conveying | — | 0.095 | 40 | 0.3 | 0.14 | NO |
| Comp. Ex. 2 | Aerosil 200 | — | pneumatic conveying | — | 0.095 | 40 | 0.5 | 0.17 | NO |
| Comp. Ex. 3 | Aerosil 200 | Plough Shear Mixer | pneumatic conveying | — | 0.095 | 40 | 0.3 | 0.12 | NO |
| Comp. Ex. 4 | Aerosil 200 | Plough Shear Mixer | pneumatic conveying | — | 0.095 | 40 | 0.3 | 0.12 | NO |
| Comp. Ex. 5 | Colloidal silica | — | pneumatic conveying | — | 0.095 | 0 | 0.3 | 0.03 | NO |
| Example 7 | Aerosil 200 | — | pneumatic conveying | Plug flow | 0.21 | 40 | 0.3 | — | — |
| Comp. Ex. 6 | Aerosil 200 | — | bucket conveying | — | — | 40 | 0.3 | 0.22 | NO |
| Comp. Ex. 7 | Aerosil 200 | Plough Shear Mixer | bucket conveying | — | — | 40 | 0.3 | 0.03 | NO |
| Comp. Ex. 8 | Aerosil 200 | — | pneumatic conveying | — | 0.005 | 40 | 0.3 | 0.18 | NO |
| Example 8 | Aerosil 200 | — | pneumatic conveying | Plug flow | 0.21 | 0 | 0.3 | 0.10 | YES |
| Example 9 | Aerosil 300 | — | pneumatic conveying | — | 0.095 | 0 | 0.3 | 0.10 | YES |
| Example 10 | Aerosil 380 | — | pneumatic conveying | — | 0.095 | 0 | 0.3 | 0.09 | YES |
| Example 11 | Aerosil 200 | Plough Shear Mixer | bucket conveying | — | — | 0 | 0.3 | 0.10 | YES |

Comp. Ex.; Comparative Example

TABLE 2

| | Caking index (1 hour) (%) | Caking index (5 hour) (%) | AAP0.3 Retention rate | AAP0.3 after mixing (g/g) | Foreign matter (particles/kg) | CRC (g/g) |
|---|---|---|---|---|---|---|
| Example 1 | 0 | 9 | 100 | 27 | 0 | 34 |
| Example 2 | 0 | 0 | 96 | 26 | 0 | 34 |
| Example 3 | 13 | 45 | 100 | 28 | 0 | 34 |
| Example 4 | 10 | 45 | 100 | 27 | 0 | 34 |

TABLE 2-continued

|  | Caking index (1 hour) (%) | Caking index (5 hour) (%) | AAP0.3 Retention rate | AAP0.3 after mixing (g/g) | Foreign matter (particles/kg) | CRC (g/g) |
|---|---|---|---|---|---|---|
| Example 5 | 0 | 10 | 100 | 27 | 0 | 34 |
| Example 6 | 0 | 8 | 100 | 27 | 0 | 34 |
| Comp. Ex. 1 | 30 | 95 | 100 | 27 | 5 | 34 |
| Comp. Ex. 2 | 0 | 65 | 96 | 26 | 10 | 34 |
| Comp. Ex. 3 | 5 | 65 | 93 | 25 | 0 | 34 |
| Comp. Ex. 4 | 20 | 80 | 100 | 27 | 4 | 34 |
| Comp. Ex. 5 | 60 | 95 | — | 26 | 0 | 34 |
| Example 7 | 30 | 60 | 100 | 27 | — | 34 |
| Comp. Ex. 6 | 100 | 100 | 100 | 27 | — | 34 |
| Comp. Ex. 7 | 30 | 100 | 96 | 26 | — | 34 |
| Comp. Ex. 8 | 60 | 100 | 100 | 27 | — | 34 |
| Example 8 | 0 | 0 | 100 | 27 | — | 34 |
| Example 9 | 0 | 5 | 100 | 27 | — | 34 |
| Example 10 | 0 | 0 | 100 | 27 | — | 34 |
| Example 11 | 10 | 45 | 100 | 27 | — | 34 |

Comp. Ex.; Comparative Example

TABLE 3

|  | Mixer | Blade (rpm) | Chopper (rpm) | Stirring time (min) | Conveying type | Pressure in pressurization tank (MPa) | Entrance temperature (° C.) | Exit temperature (° C.) | Processing time (min) | Linear velocity at the end (m/sec) | Solid-Air ratio at the end (kg-Solid/kg-Air) |
|---|---|---|---|---|---|---|---|---|---|---|---|
| Example 1 | — | — | — | — | pneumatic conveying | 0.095 | 35 | 32 | 3 | 7.1 | 21.3 |
| Example 2 | — | — | — | — | pneumatic conveying | 0.095 | 35 | 32 | 3 | 7.1 | 21.3 |
| Example 3 | — | — | — | — | pneumatic conveying | 0.095 | 35 | 32 | 3 | 7.1 | 21.3 |
| Example 4 | — | — | — | — | pneumatic conveying | 0.095 | 35 | 32 | 3 | 7.1 | 21.3 |
| Example 5 | — | — | — | — | pneumatic conveying | 0.095 | 35 | 32 | 3 | 7.1 | 21.3 |
| Example 6 | — | — | — | — | pneumatic conveying | 0.095 | 35 | 32 | 3 | 7.1 | 21.3 |
| Comp. Ex. 1 | — | — | — | — | pneumatic conveying | 0.095 | 35 | 32 | 3 | 7.1 | 21.3 |
| Comp. Ex. 2 | — | — | — | — | pneumatic conveying | 0.095 | 35 | 32 | 3 | 7.1 | 21.3 |
| Comp. Ex. 3 | Plough Shear Mixer | 60 | 100 | 60 | pneumatic conveying | 0.095 | 35 | 32 | 3 | 7.1 | 21.3 |
| Comp. Ex. 4 | Plough Shear Mixer | 60 | 100 | 1 | pneumatic conveying | 0.095 | 35 | 32 | 3 | 7.1 | 21.3 |
| Comp. Ex. 5 | — | — | — | — | pneumatic conveying | 0.095 | 35 | 32 | 3 | 7.1 | 21.3 |
| Example 7 | — | — | — | — | pneumatic conveying | 0.21 | 35 | 32 | 1.5 | 5.6 | 43.8 |
| Comp. Ex. 6 | — | — | — | — | bucket conveying | — | — | — | — | — | — |
| Comp. Ex. 7 | Plough Shear Mixer | 250 | 1800 | 60 | bucket conveying | — | — | — | — | — | — |
| Comp. Ex. 8 | — | — | — | — | pneumatic conveying | 0.005 | 35 | 32 | 10 | 30 | 8 |
| Example 8 | — | — | — | — | pneumatic conveying | 0.21 | 35 | 32 | 1.5 | 7.1 | 43.8 |
| Example 9 | — | — | — | — | pneumatic conveying | 0.095 | 35 | 32 | 3 | 7.1 | 21.3 |
| Example 10 | — | — | — | — | pneumatic conveying | 0.095 | 35 | 32 | 3 | 7.1 | 21.3 |
| Example 11 | Plough Shear Mixer | 60 | 100 | 1 | bucket conveying | — | — | — | — | — | — |

Comp. Ex.; Comparative Example

Results

By comparison between Examples 1 to 6 and Comparative Example 1 and 2, it is found that in the case where content of the over cohesive particles in the additive particles is low, the weight ratio (Y) of the free additive particles is also controlled at low level. In addition, foreign matter is not observed and caking index is also suppressed at low level in the above-mentioned Examples. In particular, considerable difference in evaluation of caking index after 5 hours, which corresponds to actual situations of the production of a diaper in a high-humidity area, is observed. In the case where content of the over cohesive particles in the additive particles is low, effect (low caking index) is easily obtainable even with a small value of the addition amount (X).

In Comparative Example 3, the additive particles were forcibly mixed by using a mixer in the case where the amount of the over cohesive particles in the additive particles. In this case, although foreign matter becomes not found by the use of the mixer and caking index is also improved into a somewhat low level, absorbency against pressure (AAP0.3) lowers in the wake of damages to the water-absorbing resin particles.

In Comparative Example 4, stirring conditions of the mixer were set to mild conditions. In Comparative Example 4, foreign matter is found and caking index also becomes worse, although absorbency against pressure (AAP0.3) is improved compared to Comparative Example 3.

In Comparative Example 5, colloidal silica excelling in dispersibility was used as the additive particles. In the result of Comparative Example 5, high caking index was observed compared to Comparative Examples 1 to 4, although the weight ratio (Y) of free additive particles was low, and therefore, the additive particles were in the state of being very difficult to leave. It is contemplated that this is because an original function of the additive particles to suppress adhesion between the water-absorbing resin particles lowers despite it is difficult for the additive particles to leave as a result of so fine dispersion of the additive particles as to enter fine voids on the surface of water-absorbing resin particles By comparison between Example 7 and Comparative Example 6, it is shown that caking index lowers by adopting pneumatic transportation processing in plug flow (pressure in pressurizing tank: 0.21 MPa), while caking index does not lower even by adopting transportation with bucket conveyer.

From the results of Comparative Example 1 (pressure in pressurizing tank: 0.095 MPa) and Comparative Example 8 (pressure in pressurizing tank: 0.005 MPa), it is found that sufficient mixing is not attained and caking index seldom lowers in the case of low concentration transportation, where the form of transportation is floating flow.

In Example 11, where the amount of over cohesive particles in the additive particles was small (0%), caking index lowered, while caking index seldom lowers in Comparative Example 7, where the mixture was obtained by using Plough Shear Mixer before subjecting to transporting with bucket conveyer unlike Comparative Example 6.

In Example 8, where the amount of over cohesive particles in the additive particles was small compared to Example 7, caking index was low, which is superior to Example 1. Namely, it is shown that caking index is suppressed to a very low level by lowering the amount of over cohesive particles in the additive particles and adopting pneumatic transportation processing at a pressure of 0.1 to 1.0 MPa.

By comparison between Examples (9 and 10) and Example 1, it is shown that the weight ratio (Y) of free additive particles is controlled to a low level and caking index lowers by using Aerosil 300 or Aerosil 380 made by being crushed instead of Aerosil 200, as the additive particles. This is considered because Aerosil 300 or Aerosil 380 furnishes strong thixotropy and high thickening performance, which results in strong adhesive force to the water-absorbing resin particles.

As shown in Examples above, according to the present invention, a water-absorbing resin composition and a method for producing the same which do not involve mixing in a long term or a large amount of the additive particles, and therefore, is capable of suppressing the deterioration in absorbency against pressure and the increase in cost, and of expressing good anticking characteristics in a long term suitable for the production of a diaper (for example, 5 hours).

The present application is based on JP Application No. 2006-85637, filed on Mar. 27, 2006, and JP Application No. 2006-268936, filed on Sep. 29, 2006, wherein disclosed contents are incorporated by reference in their entirety.

What is claimed is:

1. A method for producing a water-absorbing resin composition, comprising a mixing step for mixing water-absorbing resin particles and additive particles, wherein a mixture of the water-absorbing resin particles and the additive particles is subjected to pneumatic transportation processing in plug flow, after mixing or at the same time as mixing of the water-absorbing resin particles and the additive particles, wherein the water-absorbing resin particles comprise partially neutralized cross-linked poly(meth)acrylic acid, wherein the pneumatic transportation processing is conducted under a pressure of 0.21 to 0.8 MPa, wherein an amount of over cohesive particles, having a particle diameter of equal to or larger than 1.0 mm, in the additive particles, is equal to or smaller than 15% by weight, wherein the mixture of the water-absorbing resin particles and the additive particles contains 100 parts by weight of water-absorbing resin particles and 0.01 to 1 part by weight of additive particles, wherein percent by weight of the additive particles, (X[%]), based on 100% by weight of the water-absorbing resin particles in the composition, and weight ratio of free additive particles, (Y), relative to the percent by weight, (X[%]), satisfy the following formula:

$$0.04(x)^{0.1} \leq y \leq 0.2(x)^{0.5}.$$

2. The method according to claim 1, wherein the mixture of the water-absorbing resin particles and the additive particles is subjected to pneumatic transportation processing in a heated state.

3. The method according to claim 1, wherein the pneumatic transportation processing is carried out just after mixing of the water-absorbing resin particles and the additive particles.

4. The method according to claim 1, wherein the pneumatic transportation processing is carried out after mixing without stirring of the water-absorbing resin particles and the additive particles.

5. The method according to claim 1, wherein time required for the pneumatic transportation processing is 0.1 to 20 minutes.

6. The method according to claim 1, wherein the mixture to be subjected to the pneumatic transportation processing, is heated or under heat-retention at 30 to 100° C.

7. The method according to claim 1, wherein the additive particles are water-insoluble.

8. The method according to claim 1, wherein the additive particles are amorphous silica fine particles.

9. The method according to claim 1, wherein centrifuge retention capacity of the water-absorbing resin particles to an aqueous solution of sodium chloride of 0.90% by weight is equal to or larger than 25 [g/g], and absorbency against pressure at 0.3 psi is equal to or larger than 10 [g/g].

* * * * *